United States Patent
Kim

(10) Patent No.: US 9,730,984 B2
(45) Date of Patent: Aug. 15, 2017

(54) COMPOSITION FOR PREVENTING OR TREATING RHEUMATOID ARTHRITIS

(71) Applicant: GemVax & KAEL Co., Ltd., Daejeon (KR)

(72) Inventor: Sang Jae Kim, Seoul (KR)

(73) Assignee: GEMVAX & KAEL CO., LTD. (KR)

( * ) Notice: Subject to any disclaimer, the term of this patent is extended or adjusted under 35 U.S.C. 154(b) by 0 days.

(21) Appl. No.: 14/400,324

(22) PCT Filed: May 10, 2013

(86) PCT No.: PCT/KR2013/004156
§ 371 (c)(1),
(2) Date: Mar. 3, 2015

(87) PCT Pub. No.: WO2013/169067
PCT Pub. Date: Nov. 14, 2013

(65) Prior Publication Data
US 2015/0175978 A1   Jun. 25, 2015

(30) Foreign Application Priority Data

May 11, 2012 (KR) .......... 10-2012-0050529
May 11, 2012 (KR) .......... 10-2012-0050533
Jul. 2, 2012 (KR) .......... 10-2012-0071989
Sep. 19, 2012 (KR) .......... 10-2012-0104207

(51) Int. Cl.
| | |
|---|---|
| A61K 38/00 | (2006.01) |
| A61K 38/45 | (2006.01) |
| A61K 38/10 | (2006.01) |
| A61K 9/00 | (2006.01) |
| C12N 9/12 | (2006.01) |
| A23L 33/18 | (2016.01) |

(52) U.S. Cl.
CPC .............. *A61K 38/45* (2013.01); *A23L 33/18* (2016.08); *A61K 9/0019* (2013.01); *A61K 38/10* (2013.01); *C12N 9/1276* (2013.01); *A23V 2002/00* (2013.01); *A61K 38/00* (2013.01); *C12Y 207/07049* (2013.01)

(58) Field of Classification Search
None
See application file for complete search history.

(56) References Cited

U.S. PATENT DOCUMENTS

| | | |
|---|---|---|
| 6,967,211 B2 | 11/2005 | Inoue |
| 7,030,211 B1 | 4/2006 | Gaudernack et al. |
| 7,794,723 B2 | 9/2010 | Gaudernack et al. |
| 8,828,403 B2 | 9/2014 | Filaci et al. |
| 8,933,197 B2 | 1/2015 | Stemmer et al. |
| 9,023,987 B2 | 5/2015 | Chung et al. |
| 2002/0042401 A1 | 4/2002 | Ferguson et al. |
| 2003/0027769 A1 | 2/2003 | Scialdone et al. |
| 2003/0143228 A1 | 7/2003 | Chen et al. |
| 2006/0106196 A1* | 5/2006 | Gaudernack et al. ........ 530/326 |
| 2007/0190561 A1 | 8/2007 | Morin et al. |
| 2009/0136917 A1 | 5/2009 | Szalay et al. |
| 2009/0186802 A1 | 7/2009 | Alluis et al. |
| 2009/0215852 A1 | 8/2009 | Bascomb et al. |
| 2011/0135692 A1 | 6/2011 | Filaci et al. |
| 2011/0150873 A1 | 6/2011 | Grainger |
| 2011/0183925 A1 | 7/2011 | Sato et al. |
| 2012/0065124 A1 | 3/2012 | Morishita et al. |
| 2012/0208755 A1 | 8/2012 | Leung |
| 2012/0277290 A1 | 11/2012 | Collard et al. |
| 2013/0129760 A1 | 5/2013 | Gaudernack et al. |
| 2013/0230591 A1 | 9/2013 | Fellous et al. |
| 2015/0099692 A1 | 4/2015 | Kim et al. |
| 2015/0099693 A1 | 4/2015 | Kim et al. |
| 2015/0175978 A1 | 6/2015 | Kim |
| 2015/0307859 A1 | 10/2015 | Kim |
| 2015/0343095 A1 | 12/2015 | Kim |
| 2015/0353903 A1 | 12/2015 | Kim |
| 2016/0002613 A1 | 1/2016 | Kim |
| 2016/0008438 A1 | 1/2016 | Kim |
| 2016/0082089 A1 | 3/2016 | Kim |
| 2016/0120966 A1 | 5/2016 | Kim |
| 2016/0137695 A1 | 5/2016 | Kim |
| 2016/0151512 A1 | 6/2016 | Kim |
| 2016/0250279 A1 | 9/2016 | Kim |
| 2016/0296604 A1 | 10/2016 | Kim |
| 2016/0375091 A1 | 12/2016 | Kim |

FOREIGN PATENT DOCUMENTS

| | | |
|---|---|---|
| EP | 1020190 A3 | 10/2000 |
| EP | 1093381 B2 | 7/2009 |
| EP | 1817337 B1 | 1/2011 |
| JP | 2010252810 A | 11/2010 |
| JP | 5577472 B2 | 8/2014 |

(Continued)

OTHER PUBLICATIONS

Southern Cross, downloaded online from URL:< https://www.southerncross.co.nz/AboutTheGroup/HealthResources/Medical-Library/tabid/178/vw/1/ItemID/124/Rheumatoid-arthritis-causes-symptoms-treatment.aspx>.*

(Continued)

*Primary Examiner* — James H Alstrum Acevedo
*Assistant Examiner* — Sergio Coffa
(74) *Attorney, Agent, or Firm* — Sterne, Kessler, Goldstein and Fox P.L.L.C.

(57) ABSTRACT

The present disclosure relates to a composition for treating and preventing an rheumatoid arthritis, wherein the composition containing a peptide comprising amino acid sequence of SEQ ID NO: 1, a peptide having 80% or more sequence identity with the amino acid sequence of the peptide or a peptide which is a fragment thereof. According to the present invention, provided is a composition for prevention or treatment of rheumatoid arthritis having a superior effect of treating and preventing rheumatoid arthritis with minimized side effect.

16 Claims, 10 Drawing Sheets

(56) References Cited

FOREIGN PATENT DOCUMENTS

| | | |
|---|---|---|
| KR | 20010012613 A | 2/2001 |
| KR | 20010020601 A | 3/2001 |
| KR | 10-2004-0015087 A | 2/2004 |
| KR | 20040045400 A | 6/2004 |
| KR | 20040107492 A | 12/2004 |
| KR | 20050020987 A | 3/2005 |
| KR | 20050040517 A | 5/2005 |
| KR | 20060109903 A | 10/2006 |
| KR | 20070083218 A | 8/2007 |
| KR | 20080084818 A | 9/2008 |
| KR | 20090033878 A | 4/2009 |
| KR | 20090103957 A | 10/2009 |
| KR | 20100058541 A | 6/2010 |
| KR | 20100085527 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120087885 A | 8/2012 |
| KR | 20120121196 A | 11/2012 |
| KR | 20120130996 A | 12/2012 |
| KR | 20120133661 A | 12/2012 |
| WO | WO-0002581 A1 | 1/2000 |
| WO | WO-2010003520 A2 | 1/2010 |
| WO | WO-2010012850 A1 | 2/2010 |
| WO | WO-2011101173 A1 | 8/2011 |
| WO | WO-2011150494 A1 | 12/2011 |
| WO | WO-2013100500 A1 | 7/2013 |
| WO | WO-2013118899 A1 | 8/2013 |
| WO | WO-2013135266 A1 | 9/2013 |
| WO | WO-2013167574 A1 | 11/2013 |
| WO | WO-2013169060 A1 | 11/2013 |
| WO | WO-2013169077 A1 | 11/2013 |
| WO | WO-2014010971 A1 | 1/2014 |
| WO | WO-2014046478 A1 | 3/2014 |
| WO | WO-2014046481 A1 | 3/2014 |
| WO | WO-2014046490 A1 | 3/2014 |
| WO | WO-2014171792 A1 | 10/2014 |
| WO | WO-2014196841 A1 | 12/2014 |
| WO | WO-2014204281 A1 | 12/2014 |
| WO | WO-2015060673 A1 | 4/2015 |
| WO | WO-2015076621 A1 | 5/2015 |
| WO | WO-2015093854 A1 | 6/2015 |
| WO | WO-2015156649 A1 | 10/2015 |
| WO | WO-2015167067 A1 | 11/2015 |

OTHER PUBLICATIONS

HSE, downloaded online from URL:< http://www.hse.ie/portal/eng/health/az/R/Rheumatoid-arthritis/>.*
Fujii et al, Telomerase insufficiency in rheumatoid arthritis (Proc Natl Acad Sci U S A. Mar. 17, 2009;106(11):4360-5).*
Brunsvig, P.F., et al., "Telomerase Peptide Vaccination in NSCLC: A Phase II Trial in Stage III Patients Vaccinated after Chemoradiotherapy and an 8-Year Update on a Phase I/II Trial," Clin. Cancer Res. 17(21):6847-6857, American Association for Cancer Research, United States (2011).
Dinarello, C.A., "Interleukin-1 in the pathogenesis and treatment of inflammatory diseases," Blood 117(14):3720-3732, American Society of Hematology, United States (2011).
Kim, H.-O. and Lee, S.-I., "Experimental Animal Models for Rheumatoid Arthritis: Methods and Applications," J. Rheumatic Dis. 19(4):189-195, The Korean College of Rheumatology, Republic of Korea (2012).
Kyte, J.A., "Cancer vaccination with telomerase peptide GV1001," Expert Opin. Investig. Drugs 18(5):687-694, Informa UK Ltd., England (2009).
Myers, L.K., et al., "Collagen-Induced Arthritis, an Animal Model of Autoimmunity," Life Sci. 61(19):1861-1878, Elsevier Science Inc., United States (1997).
Stevenson, C.L., "Advances in Peptide Pharmaceuticals," Curr. Pharm. Biotechnol. 10:122-137, Bentham Science Publishers Ltd., United Arab Emirates (2009).
Taylor, P.C. and Feldmann, M., "Anti-TNF biologic agents: still the therapy of choice for rheumatoid arthritis," Nat. Rev. Rheumatol. 5:578-582, Macmillan Publishers Limited, England (2009).
International Search Report for International Patent Application No. PCT/KR2013/004156, Korean Intellectual Property Office, Republic of Korea, mailed Aug. 14, 2013, 10 pages.
Written Opinion for International Patent Application No. PCT/KR2013/004156, Korean Intellectual Property Office, Republic of Korea, mailed Aug. 14, 2013, 13 pages.
International Preliminary Report on Patentability for International Patent Application No. PCT/KR2013/004156, The International Bureau of WIPO, Geneva, Switzerland, mailed Nov. 11, 2014, 15 pages.
Co-Pending, U.S. Appl. No. 14/400,293 inventor Kim, Sang Jae, filed Sep. 9, 2015 (Not Yet Published).
Co-Pending, U.S. Appl. No. 14/400,299 inventor Kim, Sang Jae, filed Aug. 26, 2015 (Not Yet Published).
International Searching Authority, International Search Report for International Application No. PCT/KR2013/004145, Korean Intellectual Property Office, Republic of Korea, mailed Aug. 14, 2013, 10 pages.
Smith, D.B. and Johnson, K.S., "Single-step Purification of Polypeptides Expressed in Escherichia coli as Fusions with Glutathione S-transferase," Gene 67(1):31-40, Elsevier, Netherlands (1988).
International Searching Authority, Written Opinion for International Application No. PCT/KR2013/004145, Korean Intellectual Property Office, Republic of Korea, mailed Aug. 14, 2013, 13 pages.
Choi, S.G., "Recent Advances in Cancer Cachexia," Journal of Korean Oncology Nursing 11(1):20-25 (2011).
Engineer, D.R. and Garcia, J.M., "Leptin in Anorexia and Cachexia Syndrome," International Journal of Peptides 2012:Article ID 287457, Hindawi Publishing Corporation, United States (2012).
Ghaneh, P., et al., "Biology and Management of Pancreatic Cancer," Gut 56(8):1134-1152, British Medical Association, England (2007).
International Searching Authority, International Search Report for International Application No. PCT/KR2013/004176, Korean Intellectual Property Office, Republic of Korea, mailed Aug. 6, 2013, 10 pages.
Kern, K.A. and Norton, J.A., "Cancer Cachexia," Journal of Parenteral and Enteral Nutrition 12(3):286-298, Sage Publications, United States (1988).
Lahdevirta, J., et al., "Elevated Levels of Circulating Cachectin/tumor Necrosis Factor in Patients with Acquired Immunodeficiency Syndrome," American Journal of Medicine 85(3):289-291, Excerpta Medica, United States (1988).
Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).
Roubenoff, R., et al., "Adjuvant Arthritis as a Model of Inflammatory Cachexia," Arthritis and Rheumatism 40(3):534-539, Wiley-Blackwell, United States (1997).
Tisdale, M.J., "Mechanisms of Cancer Cachexia," Physiological Reviews 89(2):381-410, American Physiological Society, United States (2009).
Walsmith, J. and Roubenoff, R., "Cachexia in Rheumatoid Arthritis," International Journal of Cardiology 85(1):89-99, Elsevier, Netherlands (2002).
International Searching Authority, Written Opinion for International Application No. PCT/KR2013/004176, Korean Intellectual Property Office, Republic of Korea, mailed Aug. 6, 2013, 7 pages.
Brandenburg, K., et al., "Peptide-based Treatment of Sepsis," Applied Microbiology and Biotechnology 90(3):799-808, Springer International, Germany (2011).
Dementia from Merck Manual, accessed on Jul. 29, 2009, pp. 1-17.
Mattson, M.P., "Pathways Towards and Away From Alzheimer's Disease," Nature 430(7000):631-639, Nature Publishing Group, England (2004).

(56) References Cited

OTHER PUBLICATIONS

Mcconnell, J.D., et al., "The Effect of Finasteride on the Risk of Acute Urinary Retention and the Need for Surgical Treatment Among Men with Bengin Prostatic Hyperplasia. Finasteride Long-term Efficacy and Safety Study Group," The New England Journal of Medicine 338(9):557-563, Massachusetts Medical Society, United States (1998).

Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).

Rheumatoid Arthritis from Merck Manual, accessed on Apr. 21, 2016, pp. 1-18.

Schenk, D., et al., "Immunization with Amyloid-beta Attenuates Alzheimer-disease-like Pathology in the PDAPP Mouse," Nature 400(6740):173-177, Nature Publishing Group, England (1999).

Van Coppenolle, F., et al., "Effects of Hyperprolactinemia on Rat Prostate Growth: Evidence of Androgeno-dependence," American Journal of Physiology. Endrocrinology and Metabolism 280(1):E120-E129, American Physiological Society, United States (2001).

Altschul, S.F., et al., "Basic Local Argument Alignment Search Tool," Journal of Molecular Biology 215(3):403-410, Elsevier, England (1990).

Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).

Bonaldi, T., et al., "monocytic Cells Hyperacetylate Chromatin Protein HMGB1 to Redirect it Towards Secretion," The EMBO Journal 22 (20):5551-5560, Wiley Blackwell, England (2003).

Cho, Y.J., "GemVax & Kael (082270)," Hana Daetoo Securities, Company Report, Sep. 10, 2012, 8 pages.

Co-pending U.S. Appl. No. 14/413,732, inventor Sang Jae Kim, filed Jul. 11, 2013.

Co-pending U.S. Appl. No. 14/896,358, inventor Sang Jae Kim, filed Dec. 4, 2015.

Co-pending U.S. Appl. No. 14/899,746, inventor Sang Jae Kim, filed Apr. 12, 2015.

Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).

Fire, A., et al., "Potent and Specific Genetic Interference by Double-stranded RNA in Caenorhabditis elegans," Nature 391(6669):806-811, Nature Publishing Group, England (1998).

Fittipaldi, A., et al., "Cell Membrane Lipid Rafts Mediate Caveolar Endocytosis of HIV-1 Tat Fusion Proteins," Journal of Biological Chemistry 278(36):34141-34149, American Society for Biochemistry and Molecular Biology, United States (2003).

Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).

GemVax Receives Report on Anti-Inflammatory Mechanism, The Asia Economy Daily, Article written on May 7, 2013.

Granger, D.N. and Korthuis, R.J., "Physiologic Mechanisms of Postischemic Tissue Injury," Annual Review of Physiology 57:311-332, Annual Reviews, United States (1995).

Gunturu, K.S., et al., "Immunotherapy Updates in Pancreatic Cancer: Are we there yet?," Therapeutic Advances in Medical Oncology 5(1):81-89, Sage, England (2013).

Heitz, F., et al., "Twenty Years of Cell-Penetrating Peptides: From Molecular Mechanisms to Therapeutics," British Journal of Pharmacology 157(2):195-206, Wiley, England (2009).

Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor & Francis, United States (2012).

International Preliminary Report on Patentability for International Application No. PCT/EP2013/059460, International Bureau of WIPO, Switzerland, mailed Nov. 11, 2014, 5 pages.

International Preliminary Report on Patentability for International Application No. PCT/KR2013/004145, The International Bureau of WIPO, Switzerland, issued Nov. 11, 2014, 14 pages.

International Preliminary Report on Patentability for International Application No. PCT/KR2013/004176, The International Bureau of WIPO, Switzerland, issued Nov. 11, 2014, 14pages.

International Preliminary Report on Patentability for International Application No. PCT/KR2013/006218, The International Bureau of WIPO, Switzerland, issued Jan. 13, 2015,27 pages.

International Preliminary Report on Patentability for International Application No. PCT/KR2013/008438, The International Bureau of WIPO, Switzerland, issued Mar. 24, 2015, 10 pages.

International Preliminary Report on Patentability for International Application No. PCT/KR2013/008445, The International Bureau of WIPO, Switzerland, issued Mar. 24, 2015, 13 pages.

International Preliminary Report on Patentability for International Application No. PCT/KR2014/003425, The International Bureau of WIPO, Switzerland, mailed Oct. 20, 2015, 14 pages.

International Preliminary Report on Patentability for International Application No. PCT/KR2014/005031, The International Bureau of WIPO, Switzerland, issued Dec. 8, 2015, 8 pages.

International Preliminary Report on Patentability for International Application No. PCT/KR2014/005508, The International Bureau of WIPO, Switzerland, mailed Jan. 5, 2016, 14 pages.

International Search Report for International Application No. PCT/KR2014/003425, Korean Intellectual Property Office, Republic of Korea, mailed Jul. 21, 2014, 8 pages.

International Search Report for International Application No. PCT/EP2013/059460, European Patent Office, Netherlands, mailed Jul. 3, 2013, 5 pages.

International Search Report for International Application No. PCT/KR2013/006218, Korean Intellectual Property Office, Republic of Korea, mailed Sep. 26, 2013, 8 pages.

International Search Report for International Application No. PCT/KR2013/008438, Korean Intellectual Property Office, Republic of Korea, mailed Dec. 23, 2013, 8 pages.

International Search Report for International Application No. PCT/KR2013/008445, Korean Intellectual Property Office, Republic of Korea, mailed Dec. 23, 2013, 10 pages.

International Search Report for International Application No. PCT/KR2014/005031, Korean Intellectual Property Office, Republic of Korea, mailed Sep. 22, 2014, 6 pages.

International Search Report for International Application No. PCT/KR2014/005508, Korean Intellectual Property Office, Republic of Korea, mailed Oct. 14, 2014, 8 pages.

International Search Report for International Application No. PCT/KR2014/010035, Korean Intellectual Property Office, Republic of Korea, mailed Feb. 2, 2015, 8 pages.

International Search Report for International Application No. PCT/KR2013/008459, Korean Intellectual Property Office, Republic of Korea, mailed Dec. 23, 2013, 8 pages.

Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).

Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).

Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).

Martinez, P. and Blasco, M.A., "Telomeric and Extra-telomeric Roles for Telomerase and the Telomere-binding Proteins,"Nature Reviews Cancer 11(3):161-176, Nature Publishing Group, England (2011).

(56) References Cited

OTHER PUBLICATIONS

Modica-Napolitano, J.S. and Singh, K.K., "Mitochondria as Targets for Detection and Treatment of Cancer," Expert Reviews in MOlecular Medicine 4(9):1-19, Cambridge University Press, England (2002).
National Horizon Scanning Centre News on Emerging Technologies in Healthcare, GV1001 for Advanced and/or Metastatic Pancreatic Cancer, Published Apr. 2008.
NCBI, Reference Sequence: XP_003776612.1 (Jul. 17, 2012).
Novina, C.D. and Sharp, P.A., "The RNAi Revolution," Nature 430(6996):161-164, Nature Publishing Group, England (2004).
Oh, H., et al., "Telomerase Reverse Transcriptase Promotes Cardiac Muscle Cell Proliferation, Hypertrophy, and Survival," Proceedings of the National Academy of Sciences 98(18): 10308-10313, National Academy of Sciences, United States (2001).
Pearson, W.R. and Lipman, D.J., "Improved Tools for Biological Sequence Comparison," Proceedings of the National Academy of Sciences USA 85(8):2444-2448, National Academy of Sciences, United States (1988).
Rana, T.M., "Illuminating the Silence: Understanding the Structure and Function of Small RNAs," Nature Reviews. Molecular Cell Biology 8(1):23-36, Nature Publishing Group, England (2007).
Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).
Shay, J.W., and Wright, W.E., "Telomerase Therapeutics for Cancer: Challenges and New Directions," Nature Reviews. Drug Discovery 5(7):577-584, Nature Publishing Group, England (2006).
Smith, T.F. and Waterman, M.S., "Comparison of Biosequences," Advances in Applied Mathematics 2(4):482-489, Academic Press, Inc., United States (1981).
Thompson, J.D., et al., "Clustal W: Improving the Sensitivity of Progressive Multiple Sequence Alignment Through Sequence Weighting, Position-specific Gap Penalties and WeightMatrix Choice," Nucleic Acids Research 22(22):4673-4680, Oxford University Press, England (1994).
Tomari Y. and Zamore, P.D., "Perspective: Machines for RNAi," Genes and Development 19(5):517-529, Cold Spring Harbor Laboratory Press, United States (2005).
Vennela, B., et al., "Current and Future Strategies for Therapy of Pancreatic Cancer," International Journal of Research in Pharmacy and Medicine 2(3):728-740 (2012).
Written Opinion for International Application No. PCT/EP2013/059460, European Patent Office, Germany, mailed Jul. 3, 2013, 4 pages.
Written Opinion for International Application No. PCT/KR2013/006218, Korean Intellectual Property Office, Republic of Korea, mailed Sep. 26, 2013, 26 pages.
Written Opinion for International Application No. PCT/KR2013/008438, Korean Intellectual Property Office, Republic of Korea, mailed Dec. 23, 2013, 9 pages.
Written Opinion for International Application No. PCT/KR2013/008445, Korean Intellectual Property Office, Republic of Korea, mailed Dec. 23, 2013, 12 pages.
Written Opinion for International Application No. PCT/KR2014/005031, Korean Intellectual Property Office, Republic of Korea, mailed Sep. 22, 2014, 7 pages.
Written Opinion for International Application No. PCT/KR2014/005508, Korean Intellectual Property Office, Republic of Korea, mailed Oct. 14, 2014, 13 pages.
Written Opinion for International Application No. PCT/KR2013/008459, Korean Intellectual Property Office, Republic of Korea, mailed Dec. 23, 2013, 9 pages.
Written Opinion for International Application No. PCT/KR2014/003425, Korean Intellectual Property Office, Republic of Korea, mailed Jul. 21, 2014, 13 pages.

Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).
Co-pending U.S. Appl. No. 15/303,370, inventors Kim, Sang Jae, filed Oct. 11, 2016.
Co-pending U.S. Appl. No. 15/307,632, inventors Kim, Sang Jae, filed Oct. 28, 2016.
Co-pending U.S. Appl. No. 15/346,870, inventors Kim, Sang Jae, filed Nov. 9, 2016.
Eisenegger, C., et al., "The Role of Testosterone in Social Interaction," Trends in Cognitive Sciences 15(6):263-271, Elsevier Science, England (2011).
"Seoul National University Bundang Hospital excited because of '000'," Clinical trials of Dream Anticancer Drug without side effects with Kael & GemVax, 4 pages, Apr. 22, 2013.
Gong, W., et al., "Invasion Potential of H22 Hepatocarcinoma Cells is Increased by HMGB1-induced Tumor NF-κB Signaling via Initiation of HSP70," Oncology Reports 30(3):1249-1256, D.A. Spandidos, Greece (2013).
Guo, R.F., et al., "Regulatory Effects of Eotaxin on Acute Lung Inflammatory Injury," Journal of Immunology 166(8):5208-5218, American Association of Immunologists, United States (2001).
Heldin, C.H., et al., "TGF-Beta Signalling from Cell Membrane to Nucleus through SMAD Proteins," Nature 390(6659):465-471, Nature Publishing Group, England (1997).
International Preliminary Report on Patentability for Application No. PCT/KR2014/004752, The International Bureau of WIPO, Switzerland, issued Nov. 1, 2016, 23 pages.
International Preliminary Report on Patentability for Application No. PCT/KR2015/003642, The International Bureau of WIPO, Switzerland, issued Oct. 12, 2016, 18 pages.
International Preliminary Report on Patentability for International Application No. PCT/KR2014/010035, Korean Intellectual Property Office, Republic of Korea, mailed Apr. 26, 2016, 13 pages.
International Search Report for International Application No. PCT/KR2014/004752, Korean Intellectual Property Office, Republic of Korea, mailed Jan. 16, 2015, 10 pages.
International Search Report for International Application No. PCT/KR2015/003642, Korean Intellectual Property Office, Republic of Korea, mailed Jul. 3, 2015, 8 pages.
Massague, J., "Tgf-Beta Signal Transduction," Annual Review of Biochemistry 67:753-791, Annual Reviews, United States (1998).
Morshita, M., and Peppas, N.A., "Is the Oral Route Possible for Peptide and Protein Drug Delivery?," Drug Discovery Today 11(19-20):905-910, Elsevier Science Ltd., England (2006).
National Institute of Diabetes and Digestive and Kidney Diseases, "Prostate Enlargement: Benign Prostatic Hyperplasia," Updated Sep. 2014, 14 pages.
Shaw, V.E., et al., "Current Status of GV1001 and Other Telomerase Vaccination Strategies in the Treatment of Cancer," Expert Review of Vaccines 9(9):1007-1016, Taylor & Francis, England (2010).
Song, J., et al., "Characterization and Fate of Telomerase-Expressing Epithelia during Kidney Repair," Journal of the American Society of Nephrology 22(12):2256-2265, American Society of Nephrology, United States (2011).
Sasada, A, et al. "A case of elderly patient with lung cancer efficiently treated with Dendritic Cell Immunotherapy," The 20th International Congress of Personalized Medicine, Conference Program and Abstracts, Personalized Medicine Universe (Japanese edition) 4(Supplement 1): 2 pages, May 24, 2015.
Wang, W., et al., "Alleviating the Ischemia-Reperfusion Injury of Donor Liver by Transfection of Exogenous hTERT Genes," Transplantation Proceedings 41(5):1499-1503, Elsevier Science, United States (2009).
Written Opinion for International Application No. PCT/KR2014/004752, Korean Intellectual Property Office, Republic of Korea, mailed Jan. 16, 2015, 21 pages.
Written Opinion for International Application No. PCT/KR2014/010035, Korean Intellectual Property Office, Republic of Korea, mailed Feb. 2, 2015, 11 pages.

(56) References Cited

OTHER PUBLICATIONS

Written Opinion for International Application No. PCT/KR2015/003642, Korean Intellectual Property Office, Republic of Korea, mailed Jul. 3, 2015, 16 pages.

Yi, A., et al., "Radiation-Induced Complications after Breast Cancer Radiation Therapy: a Pictoral Review of Multimodality Imaging Findings," Korean Journal of Radiology 10(5):496-507, Korean Society of Radiology, Korea (2009).

Zhang, H., et al., "Inhibiting TGFβ1 has a Protective Effect on Mouse Bone Marrow Suppression Following Ionizing Radiation Exposure in Vitro," Journal of Radiation Research 54(4):630-636, Oxford University Press, England (2013).

Kawasaki, H, et al. "Detection and evaluation of activation of various cancer antigenic peptide-specific CTLs in mature dendritic cells used for dendritic cell therapy," The 21st International Congress of Personalized Medicine, Conference Program and Abstracts, Personalized Medicine Universe (Japanese edition) 4(Supplement 2): 5 pages, Oct. 17, 2015.

Beer, T.M., et al., "Phase II Study of Weekly Docetaxel in Symptomatic Androgen-independent Prostate Cancer," Annals of Oncology 12(9):1273-1279, Oxford University Press, England (2001).

Bohonowych, J.E., et al., "Comparative Analysis of Novel and Conventional HSP90 Inhibitors on HIF Activity and Angiogenic Potential in Clear Cell Renal Cell Carcinoma: Implications for Clinical Evaluation," BMC Cancer 11:520, BioMed Central, England (2011).

Bruns, A.F., et al., "A Heat-shock Protein Axis Regulates VEGFR2 Proteolysis, Blood Vessel Development and Repair," PloS One 7(11):e48539, Public Library of Science, United States (2012).

Calderwood, S.K., et al., "Heat Shock Proteins in Cancer: Chaperones of Tumorigenesis," Trends in Biochemical Sciences 31(3):164-172, Elsevier Trends Journals, England (2006).

Dempsey, N.C., et al., "Differential Heat Shock Protein Localization in Chronic Lymphocytic Leukemia," Journal of Leukocyte Biology, United States (2010).

Du, R., et al., "HIF1alpha Induces the Recruitment of Bone Marrow-derived Vascular Modulatory Cells to Regulate Tumor Angiogenesis and Invasion," Cancer Cell 13(3):206-220, Cell Press, United States (2008).

Eustace, B.K. and Jay, D.G., "Extracellular Roles for the Molecular Chaperone, Hsp90," Cell Cycle 3(9):1098-1100, Taylor & Francis, United States (2004).

Eustace, B.K. and Jay, D.G., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).

Evans, C.G., et al., "Heat Shock Protein 70 (Hsp70) as an Emerging Drug Target," Journal of Medicinal Chemistry 53(12):4585-4602, American Chemical Society, United States (2010).

Ferrarini, M., et al., "Unusual Expression and Localization of Heat-shock Proteins in Human Tumor Cells," International Journal of Cancer51(4):613-619, Wiley-Liss, United States (1992).

Garcia-Carbonero, R., et al., "Inhibition of HSP90 Molecular Chaperones: Moving Into the Clinic," The Lancet Oncology 14(9):e358-e369, Lancet Publishing Group, England (2013).

Henry, J.Y., et al., "Lenalidomide Enhances the Anti-prostate Cancer Activity of Docetaxel in vitro and in vivo," The Prostate 72(8):856-867, Wiley-Liss, United States (2012).

International Preliminary Report on Patentability for International Application No. PCT/KR2014/011280, The International Bureau of WIPO, Geneva, Switzerland, dated May 24, 2016, 15 pages.

International Search Report for International Application No. PCT/KR2014/011280, Korean Intellectual Property Office, Republic of Korea, dated Feb. 11, 2015, 12 pages.

International Search Report for International Application No. PCT/KR2014/012502, Korean Intellectual Property Office, Republic of Korea, dated Mar. 11, 2015, 10 pages.

International Preliminary Report on Patentability for International Application No. PCT/KR2014/012502, The International Bureau of WIPO, Geneva, Switzerland, dated Jun. 21, 2016, 22 pages.

Jaattela, M., "Over-expression of Hsp70 Confers Tumorigenicity to Mouse Fibrosarcoma Cells," International Journal of Cancer 60(5):689-693, Wiley-Liss, United States (1995).

Jemal, A., et al., "Cancer Statistics, 2008," CA: A Cancer Journal of Clinicians 58(2):71-96, Wiley, United States (2008).

Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).

Kocsis, J., et al., "Serum Level of Soluble 70-kD Heat Shock Protein Is Associated With High Mortality in Patients With Colorectal Cancer Without Distant Metastasis," Cell Stress & Chaperones 15(2):143-151, Springer, Netherlands (2010).

Liu, Q.J., et al., "Rapamycin Enhances the Susceptibility of Both Androgen-dependent and—independent Prostate Carcinoma Cells to Docetaxel," Chinese Medical Journal 123(3):356-360, Chinese Medical Association, China (2010).

Morano, K.A., "New Tricks for an Old Dog: the Evolving World of Hsp70," Annals of the New York Academy of Sciences 1113:1-14, Blackwell, United States (2007).

Murphy, M.E., "The Hsp70 Family and Cancer," Carcinogenesis 34(6):1181-1188, Irl Press, England (2013).

Nagaraju, G.P., et al., "Antiangiogenic Effects of Ganetespib in Colorectal Cancer Mediated Through Inhibition of HIF-1α and STAT-3," Angiogenesis 16(4):903-917, Springer, Germany (2013).

Pfosser, A., et al., "Liposomal HSP90 Cdna Induces Neovascularization via Nitric Oxide in Chronic Ischemia," Cardiovascular Research65(3):728-736, Oxford Journals, England (2005).

Powers, M.V., et al., "Targeting HSP70: the Second Potentially Druggable Heat Shock Protein and Molecular Chaperone?," Cell Cycle 9(8):1542-1550, Taylor & Francis, United States (2010).

Sayers, S., et al., "Vaxjo: A Web-based Vaccine Adjuvant Database and its Application for Analysis of Vaccine Adjuvants and their Uses and their Uses in Vaccine Development," Journal of Biomedicine and Biotechnology 2012:1-13, Article ID 831486, Hindawi Publishing Corporation, United States (2012).

Seo, J.S., et al., "T Cell Lymphoma in Transgenic Mice Expressing the Human Hsp70 Gene," Biochemical and Biophysical Research Communications 218(2):582-587, Elsevier, United States (1996).

Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).

Uehara, Y., "Natural Product Origins of Hsp90 Inhibitors," Current Cancer Drug Targets 3(5):325-330, Bentham Science Publishers, Netherlands (2003).

Vanbuskirk, A., et al., "A Peptide Binding Protein Having a Role in Antigen Presentation Is a Member of the HSP70 Heat Shock Family," The Journal of Experimental Medicine 170(6):1799-1809, Rockefeller University Press, United States (1989).

Volloch, V.Z. and Sherman, M.Y., "Oncogenic Potential of Hsp72," Oncogene 18(24):3648-3651, Nature Publishing Group, England (1999).

Written Opinion for International Application No. PCT/KR2014/011280, Korean Intellectual Property Office, Republic of Korea, dated Feb. 11, 2015, 14 pages.

Written Opinion for International Application No. PCT/KR2014/012502, Korean Intellectual Property Office, Republic of Korea, dated Mar. 11, 2015, 20 pages.

Yeh, C.H., et al., "Clinical Correlation of Circulating Heat Shock Protein 70 in Acute Leukemia," Leukemia Research 34(5):605-609, Pergamon Press, England (2010).

Zhou, J., et al., "PI3K/Akt Is Required for Heat Shock Proteins to Protect Hypoxia-inducible Factor 1alpha From pVHL-independent Degradation," The Journal of Biological Chemistry 279(14):13596-13513, American Society for Biochemistry and Molecular Biology, United States (2004).

\* cited by examiner

SEQUENCE LISTING

<160> NUMBER OF SEQ ID NOS: 2

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
                100                 105                 110

Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
        130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
                180                 185                 190

Pro Arg Arg Arg Leu Gly Cys Glu Arg Ala Trp Asn His Ser Val Arg
            195                 200                 205

Glu Ala Gly Val Pro Leu Gly Leu Pro Ala Pro Gly Ala Arg Arg Arg
        210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
                260                 265                 270

Val Ser Pro Ala Arg Pro Ala Glu Glu Ala Thr Ser Leu Glu Gly Ala
            275                 280                 285

Leu Ser Gly Thr Arg His Ser His Pro Ser Val Gly Arg Gln His His
        290                 295                 300

```
Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
            325                 330                 335

Asp Lys Glu Gln Leu Arg Pro Ser Phe Leu Ser Ser Leu Arg Pro
        340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
        370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
            405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
            485                 490                 495

Leu Gly Lys His Ala Lys Leu Ser Leu Gln Glu Leu Thr Trp Lys Met
        500                 505                 510

Ser Val Arg Asp Cys Ala Trp Leu Arg Arg Ser Pro Gly Val Gly Cys
    515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
            565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
            645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
        690                 695                 700

Glu Leu Tyr Phe Val Lys Val Asp Val Thr Gly Ala Tyr Asp Thr Ile
705                 710                 715                 720
```

-continued

```
Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110
```

```
Ala Leu Glu Ala Ala Ala Asn Pro Ala Leu Pro Ser Asp Phe Lys
    1115                1120            1125

Thr Ile Leu Asp
    1130
```

COMPOSITION FOR PREVENTING OR TREATING RHEUMATOID ARTHRITIS

REFERENCE TO SEQUENCE LISTING SUBMITTED ELECTRONICALLY VIA EFS-WEB

The content of the electronically submitted sequence listing (Name 2473_0770004_SeqListing_ST25.txt; Size: 10,430 bytes; and Date of Creation: Mar. 3, 2015) filed on Mar. 3, 2015, is incorporated herein by reference in its entirety.

TECHNICAL FIELD

The present invention relates to a composition for prevention and treatment of rheumatoid arthritis comprising: a peptide containing an amino acid sequence of sequence number 1; and a peptide which is at least 80% homologous to the peptide sequence, or a peptide which is a fragment thereof.

BACKGROUND ART

Rheumatoid arthritis is chronic inflammatory disease characterized by multiple arthritis. In initial stage an inflammation occurs in synovial membrane covering a joint but it spreads across the surrounding cartilages and bones to destroy and modify the joint. Besides joint, other symptoms out of the joint comprise anemia, Sjogren's syndrome, subcutaneous nodule, pulmonary fibrosis, vasculitis, skin ulcer as disease able to do systemic invasion.

The exact cause of rheumatoid arthritis has not found yet, but autoimmunity has been known as a major mechanism thereof. The autoimmunity means a disorder of an immune system attacking itself rather than protecting from outside. Generally a genetic factor and an infection of bacteria or virus have been regarded as the cause of rheumatoid arthritis. Rheumatoid arthritis has been commonly known as the disease which easily occurs after getting stressed physically or psychologically. In other words, rheumatoid arthritis is an inveterate autoimmune disease involving a swelling, an inflammation, stiff and a pain in a joint and showing a systemic multiple arthritis symptom in whole body. In other words, it means a systematic disease that the body regards itself as nonself, attacks itself based on a defect of recognizing self-nonself and generates an abnormal immune response making an inflammation of connective tissue.

Degenerative arthritis, namely osteoarthritis means a disease. When an aging and degeneration arise in chondrocytes consisting a cartilage, synthesizing type II collagen and proteoglycan are inhibited and simultaneously creating inflammatory cytokines comprising interleukin-1β and tumor necrosis factor-α are induced and then a synthesis and an activity of matrix metalloproteinase (MMP) which degrades joint matrix are increased so that the destructed cartilage tissue causes the disease.

Furthermore, rheumatoid arthritis is worsened by an acceleration of degrading joint matrix when much more MMP synthesis is induced by production of a nitrogen monoxide causing a synthesis of self-amplified inflammatory cytokines. At the same time, the inflammatory cytokines induce an inflammation at arthritis by increasing production of prostaglandin E2 which is a lipid metabolite.

As therapies for chronic joint rheumatism, anti-inflammatory steroid (e.g. prednisolon), non-steroidal anti-inflammatory drug (e.g. indomethacin, aspirin), immunosuppressant (e.g. cyclosporine A, tacrolimus (FK506), methotrexate, cyclophosphamide, azathioprene), disease modification anti-rheumatism drug (e.g. gold salt reagent) are used. Anti-inflammatory drugs control an inflammation and reduce a pain and swelling, but it is difficult to inhibit a progress of disease. Therefore, most of drugs simply alleviate symptoms or delay a progress of a disease and also have a probability of expressing side effect in long-term administration so no drug can be said enough to be satisfiable.

On the other hand, drugs for treatment of rheumatoid arthritis could be classified based on major mechanisms of a reduce of an inflammation, a delay of a disease progress and a decline of a uric acid concentration, and many drugs for treatment of neural joint reduce an inflammation. The inflammation is a pathological progress causing a pain, an edema, a fever, a seizure and a stiff, and drugs to ease the inflammation rapidly comprise non-steroid anti-inflammatory drug comprising aspirin and steroid anti-inflammatory drug comprising cortisone.

Non-steroid anti-inflammatory drug has an effect to relieve an inflammation and to ease neural joint by reducing a pain, but the drug is prohibited for a person who has an active peptic ulcer and a history of bleeding in stomach area because the drug may cause a gastro enteric trouble and a stomachache. Steroid anti-inflammatory drug is not used commonly because the drug has a severe side effect comprising a weight gain and a hypertension compared to its effectiveness. Particularly, steroid anti-inflammatory drug is irrelevant to a radical therapy and the drug may lead to over-use because of a reduction in a pain temporarily, so there is need to care to use the drug which may cause a destruction of neural joint and an aggravation of a disease.

Therefore, because existing therapies used to treat arthritis have a limited effectiveness of treatment and also involve a side effect, the existing therapies have a problem that they are not be able to be used in the long term. So, new therapy that can solve problems in the existing therapies has been needed.

PRIOR ART

Patents

KR 2012-0121196 A
KR 2004-0015078 A

Non-Patents

Kim et al., "Experimental Animal Models for Rheumatoid Arthritis: Methods and Applications", Journal of Rheumatic Disease, Vol. 19, No. 4, August 2012

Myers et al., "Collagen-Induced Arthritis, an Animal Model of Autoimmunity", Life Sciences, Vol. 61, No. 19, pp. 1861-1878, 1997

DISCLOSURE

Technical Problem

The inventors of the present disclosure have made efforts to develop a composition effective in treating rheumatoid arthritis without harmful side effects and have completed the present disclosure.

The present disclosure is directed to providing a composition effective in treating rheumatoid arthritis comprising a peptide derived from a telomerase.

Technical Solution

According to one embodiments of the present invention, provided is a composition for prevention and treatment of rheumatoid arthritis comprising a peptide that comprises an amino acid sequence of SEQ ID No: 1, a peptide comprising an amino acid sequence having a sequence identity of 80% or greater to the amino acid sequence, or a peptide fragment of the above-mentioned peptides.

In a composition for prevention and treatment of rheumatoid arthritis according to an embodiment of the present invention, the peptide fragment comprises three or more amino acids In a composition for prevention and treatment of rheumatoid arthritis according to an embodiment of the present invention, the peptide may be derived from human telomerase.

In a composition for prevention and treatment of rheumatoid arthritis according to an embodiment of the present invention, the composition may eliminate, prevent or treat symptoms related to rheumatoid arthritis in substance.

In a composition for prevention and treatment of rheumatoid arthritis according to an embodiment of the present invention, the composition may be provided in the solution concentration that is 5 nM/Kg or less, more desirably that is from 0.15 nM/kg to 5 nM/kg.

In a composition for prevention and treatment of rheumatoid arthritis according to an embodiment of the present invention, the composition may be an external skin composition.

In a composition for prevention and treatment of rheumatoid arthritis according to an embodiment of the present invention, the composition may be a pharmaceutical composition.

In a composition for prevention and treatment of rheumatoid arthritis according to an embodiment of the present invention, the composition may be a food composition.

According to one embodiments of the present invention, provided is a method of prevention and treatment of rheumatoid arthritis, the method comprises the step of administering an effective amount of the composition for prevention and treatment of rheumatoid arthritis to a subject in need thereof.

In a method for prevention and treatment of rheumatoid arthritis according to an embodiment of the present invention, the composition may be administered by below 5 nM/Kg/day, more preferably from 0.15 nM/Kg/day to 5 nM/Kg/day.

According to one embodiments of the present invention, provided is a use of the composition for prevention and treatment of rheumatoid arthritis.

In one embodiment, provided is a kit for prevention and treatment of rheumatoid arthritis comprising a peptide comprising an amino acid sequence of SEQ ID No: 1, a peptide comprising an amino acid sequence having a sequence identity of 80% or greater to the amino acid sequence, or a peptide fragment of the above-mentioned peptides; and instructions at least one of administration dose, administration route, administration frequency, and indication of the peptide or composition.

Advantageous Effects

According to the present invention, a composition having a good effectiveness to prevent or treat rheumatoid arthritis in minimized side effect may be provided.

BEST MODE

Figure 1:
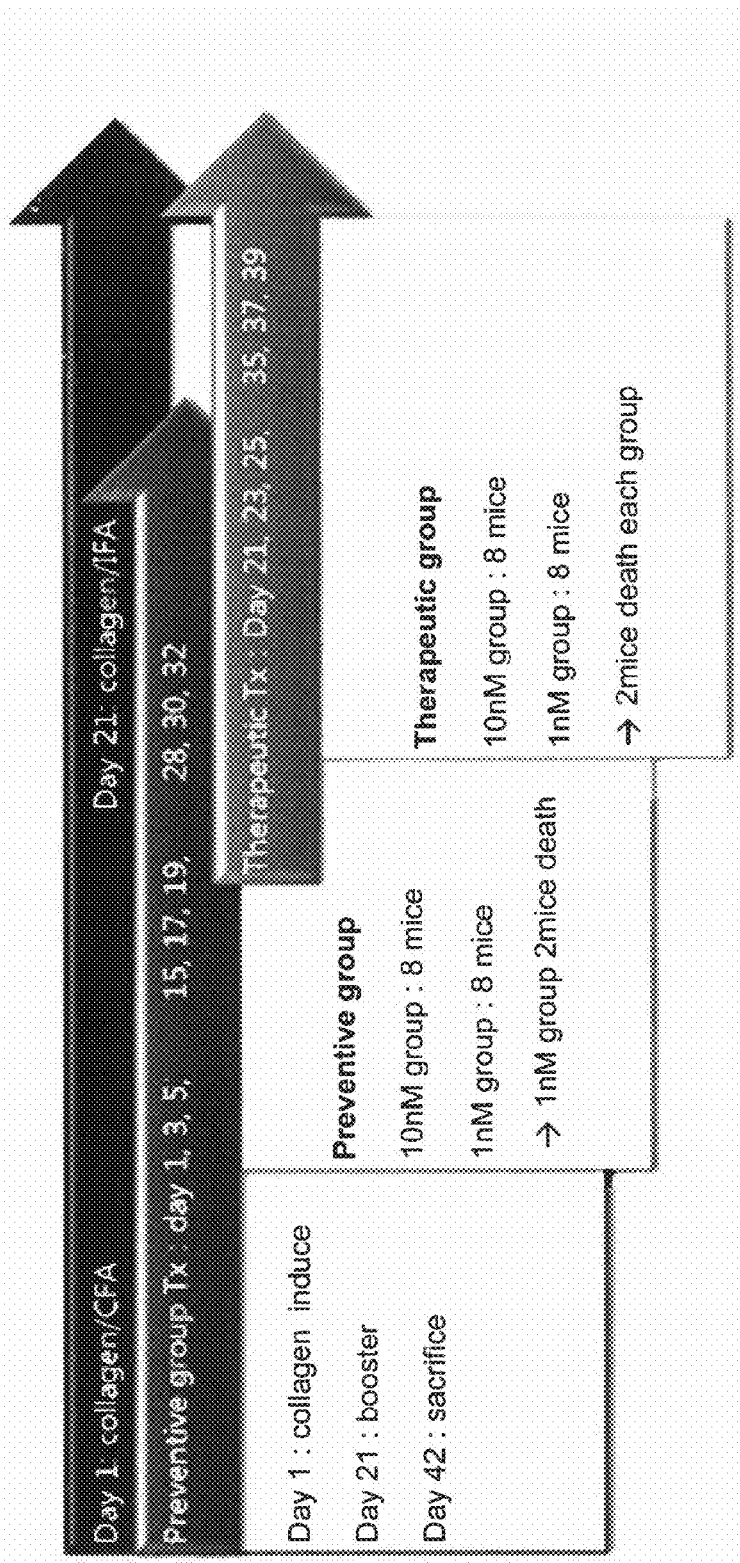
FIG. 1 and FIG. 2 show schedules according to the time for the first and second experiments of inducing rheumatoid arthritis and treating peptides by using CIA animal models respectively.

The present disclosure can be modified and embodied in various ways. Hereinafter, the present disclosure will be described in more detail through exemplary embodiments. However, the following examples are not intended to be limitative of the present disclosure. Rather, the present disclosure can be variously changed based on the appended claims. It is to be understood that the present disclosure comprises any change, equivalent or substitute that falls within the technical idea and scope of the present disclosure. In the description, details of well-known features and techniques may be omitted to avoid unnecessarily obscuring the presented embodiments.

Telomere is known as a repetitive sequence of genetic material found at the ends of chromosomes that prevent chromosomes from damage or merging onto other chromosomes. The length of the telomere is shortened at each cell division, and after a certain number of cell division, the telomere length is extremely shortened to the extent in which the cell stops dividing and dies. On the other hand, the elongation of telomeres is known to extend the life span of a cell. For an example, cancer cells excrete an enzyme called telomerase, which prevents shortening of telomeres, thus resulting in proliferation of cancer cells.

In one embodiment of the present invention, polynucleotide encoding a peptide, wherein the peptide comprises amino acid sequence of SEQ ID NO: 1, the peptide has above 80% homology with SEQ ID NO: 1, or the peptide is a fragment of above-mentioned peptides, is provided. The polynucleotide mentioned above enables production of the peptides in large quantities. For example, cultivation of vectors that include polynucleotides encoding peptides allows production of peptides in large quantities.

The peptides disclosed herein may include peptides comprising an amino acid sequence at least 80%, at least 85%, at least 90%, at least 95%, at least 96%, at least 97%, at least 98%, at least 99% of sequence homology with the peptide of SEQ ID NO 1 or a fragment thereof. Moreover, the peptides disclosed in the present invention may include peptides having differences from SEQ ID NO: 1 or a fragment thereof in at least one amino acids, at least 2 amino acids, at least 3 amino acids, at least 4 amino acids, at least 5 transformed amino acids, at least 6 transformed amino acids, or at least 7 amino acids.

In one embodiment of the present invention, changes in amino acids include modifications of peptide's physical and chemical characteristics. For example, amino acid modification can be performed for improving thermal stability of the peptide, altering substrate specificity, and changing the optimal pH.

In an exemplary embodiment of the present disclosure, a peptide of SEQ ID NO 1, a peptide which is a fragment of the peptide of SEQ ID NO 1 or a peptide having 80% or more sequence identity with the peptides comprises a peptide derived from telomerase, specifically human (Homo sapiens) telomerase.

The term "amino acid" herein comprises not only the 22 standard amino acids that are naturally integrated into a peptide but also the D-isomers and modified amino acids. Therefore, in a specific embodiment of the present invention, a peptide herein comprises a peptide having D-amino acids. On the other hand, a peptide may include non-standard amino acids such as those that have been post-translationally modified. Examples of post-translational modification include phosphorylation, glycosylation, acylation(comprising acetylation, myristorylation, plamitoylation), alkylation, carboxylation, hydroxylation, glycation, biotinylation, ubiquitinylation, modification in chemical properties (e.g. β-removing deimidation, deamidation) and structural modification (e.g. formation of disulfide bridge). Also, changes of amino acids include the changes of amino acids that occur due to chemical reaction during the combination process with cross-linkers for formation of a peptide conjugate, such as changes in an amino group, carboxyl group or side chain.

A peptide disclosed herein may be a wild-type peptide that has been identified and isolated from natural sources. On the other hand, when compared to SEQ ID NO: 1 or its fragments, the peptides disclosed herein may be artificial variants that comprise one or more amino acids substituted, deleted and/or inserted. Amino acid alteration in wild-type polypeptides—not only in artificial variants—comprises protein folding and/or conservative substitutions of amino acids that do not influence activities significantly. Examples of conservative substitutions may be within the groups of basic amino acids (arginine, lysine and histidine), acidic amino acids (glutamic acid and aspartic acid), polar amino acids (glutamine and asparagines), hydrophobic amino acids (leucine, isoleucine, valine and methionine), aromatic amino acids (phenylalanine, tryptophan and tyrosine), and small amino acids (glycine, alanine, serine, and threonine). The amino acid substitutions that do not generally alter the specific activities are known in the art. Most common occurring alterations are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and the opposite alterations thereof. Other examples of conservative substitutions are shown in the following table 2.

TABLE 1

| Original amino acid | Examples of residue substitution | Preferable residue substitution |
|---|---|---|
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | ala | Ala |
| Ser (S) | thr | Thr |
| Thr (T) | ser | Ser |
| Trp (W) | tyr; phe | Tyr |
| Tyr (Y) | trp; phe; thr; ser | Phe |
| Val (V) | ile; leu; met; phe; ala; norleucine | Leu |

The substantial modification of the biological properties of peptides are performed by selecting significantly different substitution in the following efficacies: (a) the efficacy in maintaining the structure of the polypeptide backbone in the area of substitution, such as sheet or helical three-dimensional structures, (b) the efficacy in maintaining electrical charge or hydrophobicity of the molecule in a target area, or (c) the efficacy of maintaining the bulk of the side chain. Natural residues are divided into groups by general side chain properties as the following:
  (1) hydrophobicity: Norleucine, met, ala, val, leu, ile;
  (2) neutral hydrophilicity: cys, ser, thr;
  (3) acidity: asp, glu;
  (4) basicity: asn, gln, his, lys arg;
  (5) residue that affects chain orientation: gly, pro; and
  (6) aromaticity: trp, tyr, phe.

Non-conservative substitutions may be performed by exchanging a member of the above classes with that of different classes. Any cystein residues that are not related to maintaining the proper three-dimensional structure of the peptide can typically be substituted with serine, thus increasing the oxidative stability of the molecule and preventing improper cross-linkage. Conversely, improvement of stability can be achieved by adding cysteine bond(s) to the peptide.

Another type of amino acid variants of peptides are those having a changed pattern of peptide glycosylation. The term "change" herein means deletion of at least one carbohydrate residues that are found in a peptide and/or addition of at least one glycosylated residues that do not exist within a peptide Glycosylation in peptides are typically N-linked or O-linked. The term "N-linked" herein refers to that carbohydrate residues are attached to the side chain of asparagine residues. As tripeptide sequences, asparagine-X-serine and asparagine-X-threonine (wherein the X is any amino acid except proline) are a recognition sequence for attaching a carbohydrate residue enzymatically to the side chain of asparagine. Therefore, with the presence of one of these tripeptide sequences in a polypeptide, the potential glycosylation sites are created. "O-linked glycosylation" means attaching one of sugar acetylgalactosamine, galactose, or xylose to hydroxyl amino acids. The hydroxyl amino acids are most typically serine or threonine, but 5-hydroxyproline or 5-hydroxylysine can be used.

Addition of glycosylation site to a peptide is conveniently performed by changing an amino acid sequence to contain the tripeptide sequence mentioned above (for N-linked glycosylation sites). These changes may be made by addition of at least one serine or threonine residues to the first peptide sequence, or by substitution with those residues (for O-linked glycosylation sites).

In one embodiment of the present invention, a polynucleotide is a nucleic acid molecule that can be spontaneous or artificial DNA or RNA molecules, either single-stranded or double-stranded. The nucleic acid molecule can be one or more nucleic acids of same type (for example, having a same nucleotide sequence) or nucleic acids of different types. The nucleic acid molecules comprise one or more DNA, cDNA, decoy DNA, RNA, siRNA, miRNA shRNA, stRNA, snoRNA, snRNA PNA, antisense oligomer, plasmid and other modified nucleic acids, but not limited to those.

The SEQ ID No: 1 (hereinafter 'PEP 1') as used herein is a telomerase-derived peptide comprised of 16 amino acids. SEQ ID NO: 1 EARPALLTSRLRFIPK Also, in one aspect, the present invention is a peptide comprising amino acid sequence of SEQ ID NO: 1, a peptide having above 80% homology of amino acid sequence with above-mentioned sequence, or a fragment of the above-mentioned peptides has an advantage in that it has high feasibility due to its low toxicity within a cell.

In one aspect, the present invention is a composition for prevention and treatment of rheumatoid arthritis comprising, as an active ingredient, a peptide comprising amino acid sequence of SEQ ID NO: 1, a peptide having above 80% homology with above-mentioned sequence, or a fragment of the above-mentioned peptides.

In one aspect, the present invention is a method for prevention and treatment of rheumatoid arthritis comprising administration of a peptide comprising amino acid sequence of SEQ ID NO: 1, a peptide having above 80% homology with above-mentioned sequence, or a fragment of the above-mentioned peptides to a subject in need thereof.

In one aspect, the present invention is a use of a peptide for prevention and treatment of rheumatoid arthritis comprising administration of a peptide comprising amino acid sequence of SEQ ID NO: 1, a peptide having above 80% homology with above-mentioned sequence, or a fragment of the above-mentioned peptides to a subject in need thereof.

In one aspect, the present invention is a kit comprising a peptide comprising an amino acid sequence of SEQ ID No: 1, a peptide comprising an amino acid sequence having a sequence identity of 80% or greater to the amino acid sequence, or a peptide fragment of the above-mentioned peptides; and instructions at least one of administration dose, administration route, administration frequency, and indication of the peptide or composition.

In one aspect, the fragment may consist of at least 3 amino acids. In other aspects, the fragment may consist of at least 4 amino acids, at least 5 amino acids, at least 6 amino acids, at least 7 amino acids, at least 8 amino acids, at least 9 amino acids, at least 10 amino acids, at least 11 amino acids, at least 12 amino acids, at least 13 amino acids, at least 14 amino acids, or at least 15 amino acids.

In one aspect, the peptide may be derived from human telomerase. Specifically, the peptide of SEQ ID NO:1 means the peptide position in 611-626 of an entire human telomerase sequence (1132 amino acids, SEQ ID NO:2).

In one aspect, the peptide may be used for eliminating symptoms related to rheumatoid arthritis, or prevention and treatment of rheumatoid arthritis.

In one aspect, the peptide may be administered in a single dose of from 0.001 to 1 ng/kg or from 0.01 to 0.4 ng/kg. In other aspect, the dose of administering may be at least 0.001 ng/kg, at least 0.005 ng/kg, at least 0.01 ng/kg, at least 0.02 ng/kg or at least 0.03 ng/kg. In other aspect, the dose of administering may be less than 1 ng/kg, less than 0.9 ng/kg, less than 0.8 ng/kg, less than 0.7 ng/kg, less than 0.6 ng/kg, less than 0.5 ng/kg, less than 0.4 ng/kg, less than 0.3 ng/kg, less than 0.2 ng/kg.

In one aspect, the peptide may be administered in once at 1-5 days or in once at 1.5-2.5 days.

In one aspect, the composition may contain a peptide of 0.05-5 nM concentrations.

In one aspect, the composition may be formulated for injection.

According to an embodiment of the present invention, the composition may contain 0.1 μg/mg to 1 mg/mg, specifically 1 μg/mg to 0.5 mg/mg, more specifically 10 μg/mg to 0.1 mg/mg of a peptide comprising an amino acid sequence of SEQ ID NO: 1, a peptide comprising an amino acid sequence having a sequence identity of 80% or greater to the amino acid sequence, or a peptide fragment thereof. When the peptide is contained in the above-mentioned range, all the safety and stability of the composition may be satisfied and cost-effectiveness may be achieved.

According to an embodiment of the present invention, the composition may have applications to all animals comprising humans, dogs, chickens, pigs, cows, sheep, guinea pigs, and monkeys.

According to an embodiment of the present invention, a pharmaceutical composition may be administered through oral, rectal, transdermal, intravenous, intramuscular, intraperitoneal, intramedullary, epidural, or subcutaneous means.

Forms of oral administration may be, but not limited to, tablets, pills, soft or hard capsules, granules, powders, solutions, or emulsions. Forms of non-oral administration may be, but not limited to, injections, drips, lotions, ointments, gels, creams, suspensions, emulsions, suppositories, patches, or sprays.

According to an embodiment of the present invention, the pharmaceutical composition, if necessary, may contain additives, such as diluents, excipients, lubricants, binders, disintegrants, buffers, dispersants, surfactants, coloring agents, aromatics, or sweeteners. According to an embodiment of the present invention, the pharmaceutical composition may be manufactured by conventional methods of the industry in the art.

According to an embodiment of the present invention, the active ingredient of the pharmaceutical composition may vary according to the patient's age, sex, weight, pathology state and severity, administration route, or prescriber's judgment. Dosage may be determined by one of ordinary skill in the art based on the above-mentioned factors, and the daily dose may be, but is not limited to, about 0.0000001 ng/kg/day to about 10000 ng/kg/day or about 0.00001 ng/kg/day to about 100 ng/kg/day, specifically about 0.0001 ng/kg/day to about 10 ng/kg/day, and more specifically about 0.01 ng/kg/day to about 0.4 ng/kg/day. According to an embodiment of the present invention, the pharmaceutical composition may be administered, but is not limited to, 1 to 3 times per 1 to 5 days.

As a carrier, one or more of solid, half-solid or liquefied diluents, pillings and other materials for prescription is used. It is desirable to administrate the pharmaceutical composition in a single unit dosage form. The pharmaceutical composition of the present invention can be administrated by forms of oral or non-oral (e.g. injection, transrectal).

The pharmaceutical composition according to an embodiment of the present invention may be administered, but is not limited to, 1 to 3 times a day.

The external application composition according to an embodiment of the present invention may be provided in all forms appropriate for topical applications. For example, forms can be provided as solutions, emulsions obtained by dispersion of oil phase in water, emulsion obtained by dispersion of water in oil phase, suspension, solid, gel, powder, paste, foam or aerosol. These forms can be manufactured by conventional methods of the industry in the art.

The external application composition according to an embodiment of the present invention may include, within levels that won't harm the main effect, other ingredients that can desirably increase the main effect. In one embodiment of the present invention, the cosmetic composition may additionally include moisturizer, emollient agents, surfactants, UV absorbers, preservatives, fungicides, antioxidants, pH adjusting agent, organic or inorganic pigments, aromatics, cooling agent or antiperspirant. The formulation ratio of the above-mentioned ingredients can be decided by those skilled in the art within levels that won't harm the purpose and the effects of the present invention, and the formulation ratio based on total weight of the cosmetic composition can be 0.01 to 5% by weight, specifically 0.01 to 3% by weight.

In one embodiment of the present invention, food composition is not limited to forms, but for example may be granules, powder, liquid, and solid forms. Each form can be formed with ingredients commonly used in the industry appropriately chosen by those skilled in the art, in addition to the active ingredient, and can increase the effect with other ingredients.

Decision for dosage on the above-mentioned active ingredient is within the level of those skilled in the art, and daily dosage for example may be 1 μg/kg/day to 10 mg/kg/day, more specifically the 10 μg/kg/day to 1 mg/kg/day, more specifically the 50 μg/kg/day to 100 μg/kg/day, but not limited to these numbers and can vary according to age, health status, complications and other various factors.

Forms of oral administration may be, but not limited to, tablets, pills, soft or hard capsules, granules, powders, solution, or emulsion.

Forms of oral administration may be, but not limited to, solid or liquid dosage unit, for example powders, discutients, tablets, sugarcoated pills, capsules, granules, suspensions, solutions, syrups, drop agents, sublingual tablet other formulations.

Forms of powders are produced by pulverizing the compound of the present invention to an appropriate particle size. Forms of discutients are also produced by pulverizing the compound of the present invention and mixing with pharmaceutical carriers, for instance carbohydrates such as starch and mannitol pulverized to an appropriate particle size. If necessary, forms of powders may contain additives, such as excipients, preservatives, dispersants, coloring agents, aromatics or others.

Forms of granules as described above are produced by filling in a capsule shall such as gelatin capsule with forms of powders, discutients or tablets. After forms of lubricants or fluidizing agents such as colloidal silica, talk, magnesium stearate, calcium stearate, and solid polyethylene glycol are mixed to forms of powders, the operation of filling may make progress. Adding the forms of disintegrants or solubilizer such as carboxymethyl cellulose, carboxymethyl cellulose calcium, low level substituted hydroxypropyle cellulose, crosscarmellose sodium, carboxymethyl starch sodium, calcium carbonate, sodium carbonate may increase an effectiveness of a drug when the forms of capsules are taken.

Also, forms of micro powder of the present invention may be soft capsules made by dispersing in plant oil, polyethylene glycol, glycerin, and surfactant and covering with gelatin sheets.

Forms of tablet are made by adding excipients to create powder mixture, being granulation or slug, and tableting after adding lubricant.

If necessary, the dose prescription for oral administration may be a microcapsule. The prescription may also arouse time delay or sustain release by covering with sheath or dipping in polymer or wax.

Forms of non-oral administration may use injection, suppository and etc. For subcutaneous, muscle, or vein injection, a single dose unit such as forms of solution or suspension may be used. They are made by dissolving part of compound in non-toxic liquid carrier that is suitable for injection, and sterilizing the solution or suspension. In order to make the solution of injection isotonic solution, non-toxic salt or salt-solution may be added. Also, stabilizers, preservatives, emulsifiers may be used in combination.

Rectal administration may use a suppository made by dissolving the compound of the present invention in the mixture comprising solid having low melting point and being soluble or insoluble in water such as polyethylene glycol, cacao butter, semi synthetic lipid, poly ester (e.g. palmitic myristyl ester).

The composition for prevention and treatment of rheumatoid arthritis according to the present invention may be used in mixture or combination with other drugs such as anti-inflammatory steroid, non-steroidal anti-inflammatory drug, immunosuppressant, disease modification anti-rheumatism drug.

The term of "eliminate symptoms related to rheumatoid arthritis in substance (substantially)" used herein means that the symptoms are decreased by at least 96%.

The term of "treat" used herein, such as inhibition, regression, or delay of hindrance, or decreasing, suppressing, inhibiting, declining, eliminating, or improving hindrance are comprised.

The term of "symptom related to rheumatoid arthritis" used herein comprises any clinical or test signs and is not limited to feeling or observation made by a subject. The inflammation is the symptoms of rheumatoid arthritis.

The terms used herein is intended to be used to describe the embodiments, not to limit the present invention. Terms without numbers in front are not to limit the quantity but to show that there may be more than one thing of the term used. The terms "comprising", "having", "comprising" and "containing" shall be interpreted openly (i.e. "comprising but not limited to").

Mention of a numerical range is used instead of stating separate numbers within the range, so unless it is explicitly stated, the range should be construed as if all the numbers within the range are separately described herein. The end values of all the ranges are included in the range and can be combined independently.

Unless otherwise noted or clearly contradicting in context, all methods mentioned herein can be performed in a proper order. The use of any one embodiment and all embodiment, or exemplary language (e.g., "such as", "like~"), unless included in the claims, is used to more clearly describe the present invention, not to limit the scope of the present invention. Any language herein outside of the claims should not be interpreted as a necessity of the present invention. Unless defined otherwise, technical and scientific terms used herein have meanings ordinarily understood by a person skilled in the art that the present invention belongs to.

The preferred embodiments of the present invention include the best mode known to the inventors to perform the present invention. Variations in the preferred embodiments can become clear to those skilled in the art after reading the statements above. The present inventors' hope that those skilled in the art can use the variations adequately and present invention is conducted in other ways than listed herein. Thus, the present invention, as allowed by the patent law, comprises equivalents, modifications and variations thereof, of the key points of the invention stated in the appended claims. In addition, all possible variations within any combination of the above-mentioned components are included in the present invention, unless explicitly stated otherwise or contradicting in context. Although the present invention is described and shown by exemplary embodiments, those skilled in the art will understand well that there can be various changes in the form and details without departing from the spirit of the invention and range, defined by the claims below.

Hereinafter, the present disclosure will be described in detail through examples and test examples. However, the following examples and test examples are for illustrative purposes only and it will be apparent to those of ordinary skill in the art that the scope of the present disclosure is not limited by the examples and test examples.

MODE FOR INVENTION

Example 1

Synthesis of Peptide

The peptide of SEQ ID NO: 1 was synthesized according to the conventionally known method of solid phase peptide synthesis. More specifically, the peptide was synthesized by coupling each amino acid from C-terminus through Fmoc solid phase peptide synthesis, SPPS, using ASP48S (Peptron, Inc., Daejeon Republic of Korea). Those peptides with their first amino acid at the C-terminus being attached to a resin were used as follows:

NH2-Lys(Boc)-2-chloro-Trityl Resin
NH2-Ala-2-chloro-Trityl Resin
NH2-Arg(Pbf)-2-chloro-Trityl Resin All the amino acids to synthesize the peptide were protected by Fmoc at the N-terminus, and the amino acid residues were protected by Trt, Boc, t-Bu (t-butylester), Pbf (2,2,4,6,7-pentamethyl dihydro-benzofuran-5-sulfonyl) that can be dissolved in an acid. Examples include the followings:

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(trt)-OH, Fmoc-Tyr(tBu)-OH, Fmoc-Ahx-OH, Trt-Mercaptoacetic acid.

HBTU[2-(1H-Benzotriazole-1-yl)-1,1,3,3-tetramethylaminium hexafluorophosphate]/HOBT[N-Hydroxybenzotriazole]/NMM[4-Methylmorpholine] were used as the coupling reagents. Piperidine in 20% DMF was used to remove Fmoc. In order to remove the protection from residues or to separate the synthesized peptides from Resin, cleavage cocktail [TFA (trifluoroacetic acid)/TIS (triisopropylsilane)/EDT (ethanedithiol)/H2O=92.5/2.5/2.5/2.5] was used.

The peptide synthesis was performed by using solid phase scaffoled with the repetition of the following processes: starting with the amino acid protection, seperate reaction of each amino acid, washing with solvents, and deprotection. Each peptide was synthesized by using the solid phase scaffold combined to starting amino acid with the amino acid protection, reacting the corresponding amino acids separately, washing with a solvent and deprotected, and repeating the processes. Upon the release from the resin, the synthesized peptides were purified by HPLC, validated by Mass Spectrometry, and freeze-dried, and verify for synthesis by MS, and then freeze-dried.

The purity of the prepared peptide was found to be 95% or higher by high-performance liquid chromatography.

Specific peptide synthesis process is described as the following based on the synthesis process of PEP 1 which has SEQ ID: NO. 1.

1) Coupling

The amino acid (8 equivalent) protected with NH2-Lys (Boc)-2-chloro-Trityl Resin, and coupling agent HBTU(8 equivalent)/HOBt(8 equivalent.)/NMM(16 equivalent) melted in DMF were mixed together, and incubated at room temperature (RT) for 2 hr. Following the incubation, the reaction mixture was subjected to the sequential washes of DMF, MeOH, and DMF.

2) Fmoc deprotection

Piperidine in 20% DMF was added and incubated at RT for 5 minutes 2 times, then sequentially washed with DMF, MeOH and DMF.

3) Making the basic framework of peptide, NH2-E (OtBu)-A-R(Pbf)-P-A-L-L-T(tBu)-S(tBu)-R(pbf)L-R(Pbf)-F-I-P-K(Boc)-2-chloro-Trityl Resin) by repeating the above mentioned-reactions 1) and 2).

4) Cleavage: Cleavage Cocktail was added to the completely synthesized peptide, thus separating the synthesized peptide from the resin.

5) Pre-chilled diethyl ether was added into the obtained mixture, and then centrifugation was used to precipitate gathered peptide.

6) After purification by Prep-HPLC, the molecular weight was confirmed by LC/MS and lyophilized to produce in a powder form.

PEP 1 prepared by the method described in Example 1 was used to perform an experiment of effectiveness to prevention and treatment of rheumatoid arthritis.

Example 2

Inducing Rheumatoid Arthritis and Treating Peptides by Using CIA Animal Models

Establishing CIA (Collagen Induced Arthritis) Animal Model

In order to find effectiveness of the peptide according to the present invention to rheumatoid arthritis (RA), CIA (collagen induced arthritis) mouse were used to confirmation.

Non-patent document disclosed in the present invention describes about CIA animal model in detail. In reference to this, the present embodiment established the CIA animal model as follows.

In the first and second experiment mentioned below, lyophilized and formed in powder PEP1 according to the Example 1 was dissolved in 0.9% saline solution and was used. After doing amendment of the purity (purity; 97.3%, content: 85.3%) of PEP1, the solution for injection was made in each concentration with 0.9% saline solution as an additive just before an administration. Every dose was administered by the solution in an amount of 100 μL.

The First Experiment

The first induction was done to 38 mice at day 1 by using 5-weeks male DBA/1J mouse (Orient Bio Inc., Korea), and the mice were divided into the preventive group consisting of 16 mice administered by a peptide composition before CIA inducement (i.e. 8 mice of 1 nM, 100 μl (around 0.2 ng dose) and 8 mice 10 nM, 100 μl (around 2 ng dose)), the therapeutic group consisting of 16 mice administered by a peptide composition after CIA inducement (i.e. 8 mice of 1 nM, 100 μl and 8 mice of 10 nM, 100 μl), and the PBS treatment group consisting of 6 mice.

To the preventive group, the treatment was done by intradermal injection in each suitable concentration at day 2, 4, 6, 21, 23, 25, 35, 37 and 39. At day 19, the second inducement was done to 38 mice, and to the therapeutic group the treatment by intradermal injection in each suitable concentration at day 21, 23, 25, 35, 37 and 30 from day 21 (see FIG. 1).

The assessment of rheumatoid arthritis index was done at from the day of second inducement to the day 42 per every two days and the joint and serum was collected after sacrificing all mice at day 42.

During the administration of PEP1 all mice were survived.

The Second Experiment

Like the first experiment, the first inducement was done to 38 mice at day 1 by using 5-week mice, the mice were divided into the group consisting of 32 mice administered by a peptide composition before CIA inducement (8 mice of 0.2 nM, 100 μl (i.e. around 0.04 ng); 8 mice of 1 nM, 100 μl (around 0.2 ng dose); 8 mice of 2 nM, 100 μl (i.e. around 0.4 ng); 8 mice of 5 nM, 100 μl (i.e. around ing)) and the PBS treatment group consisting of 6 mice.

Figure 2:
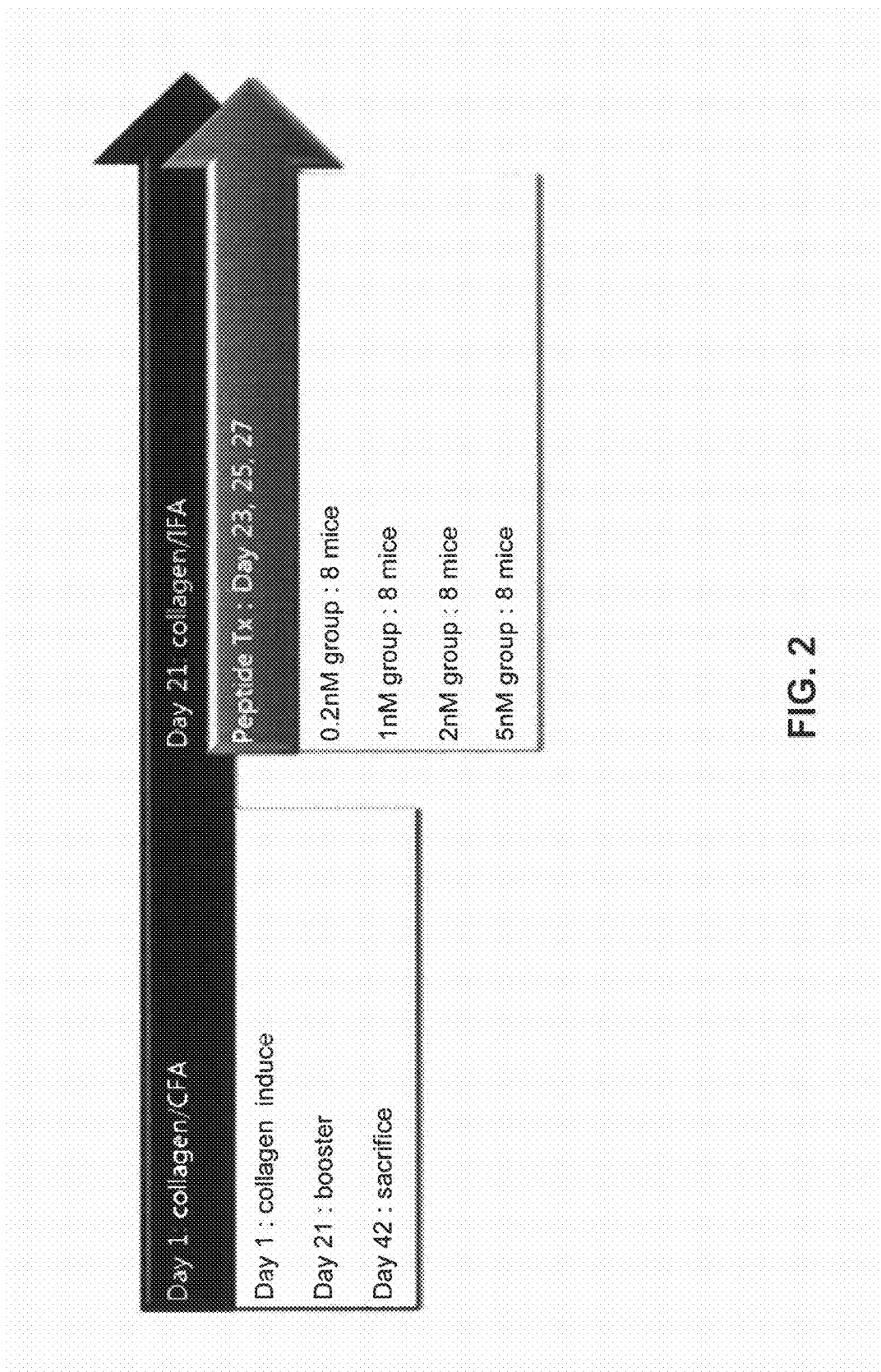

The second inducement was done at day 21, and the treatment was done by intradermal injection in each suitable concentration to each group at day 23, 25 and 27 (see FIG. 2).

The assessment of rheumatoid arthritis index was done at from the day of second inducement to the day 42 per every two days and the joint and serum was collected after sacrificing all mice at day 42.

During the administration of PEP1 all mice were survived.

Example 3

Confirming Effectiveness of Rheumatoid Arthritis

The rheumatoid arthritis index is distinguished by the point from 0 to 4, and the point given to one mouse could be from 0 to max 16 (see Table 2).

TABLE 2

The criteria of the assessment of the rheumatoid arthritis

| | |
|---|---|
| Point 0 | No aspect of rheumatoid arthritis appeared |
| Point 1 | When one toe of the five toes swelled up |
| Point 2 | When an ankle swelled up but all five toes did not swell up |
| Point 3 | When below 4 toes of the five toes and an ankle swelled up |
| Point 4 | When all five toes and an ankle swelled up |

Figure 3:
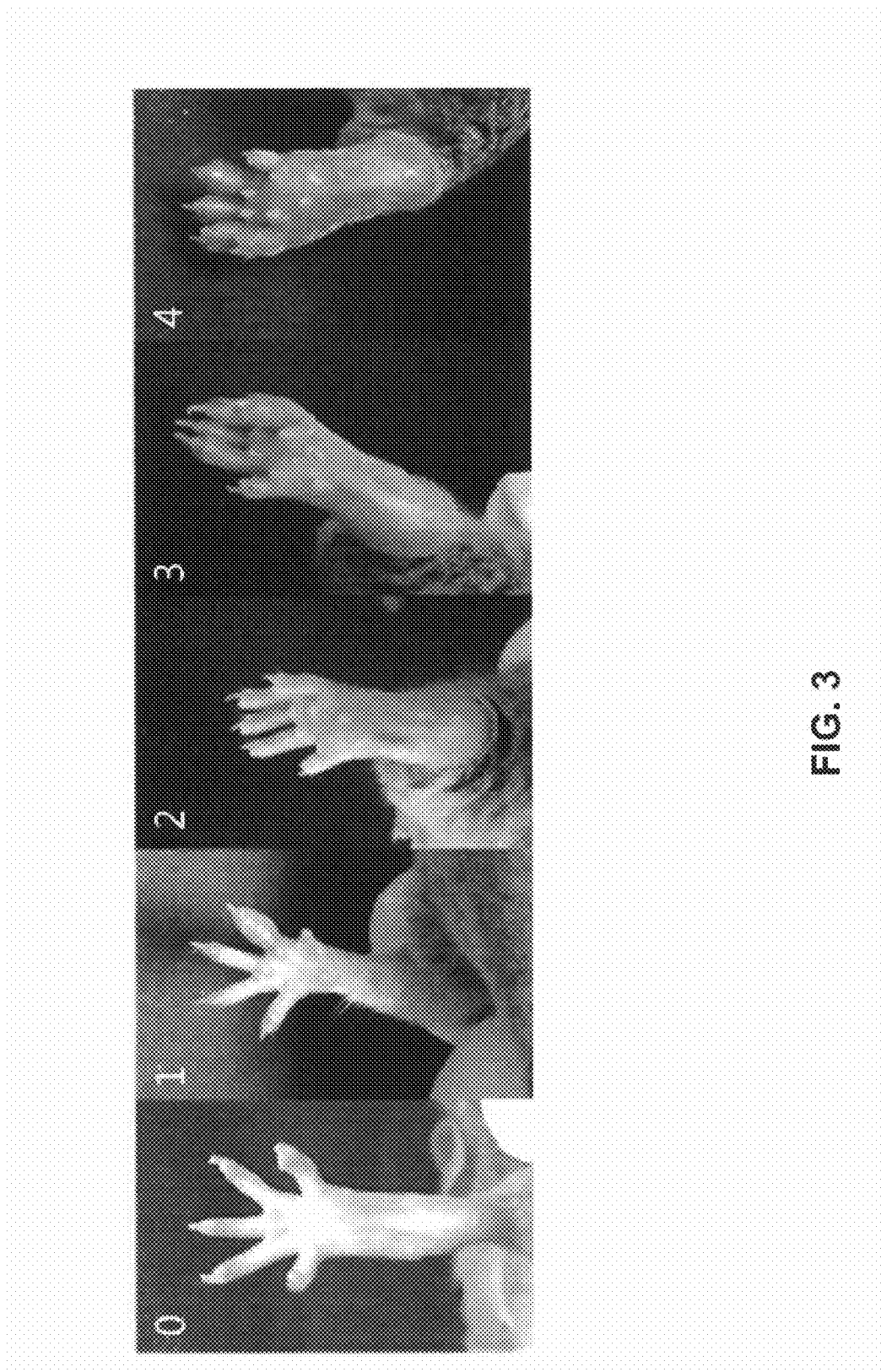
FIG. 3 shows each condition of point about rheumatoid arthritis index by a photograph.

In FIG. 3, the conditions of rheumatoid arthritis at each point described in Table 2 were shown by photograph.

For the assessment of rheumatoid arthritis, the index having point 0~16 per a mouse was measured and the points are shown by the averages thereof.

Figure 4:
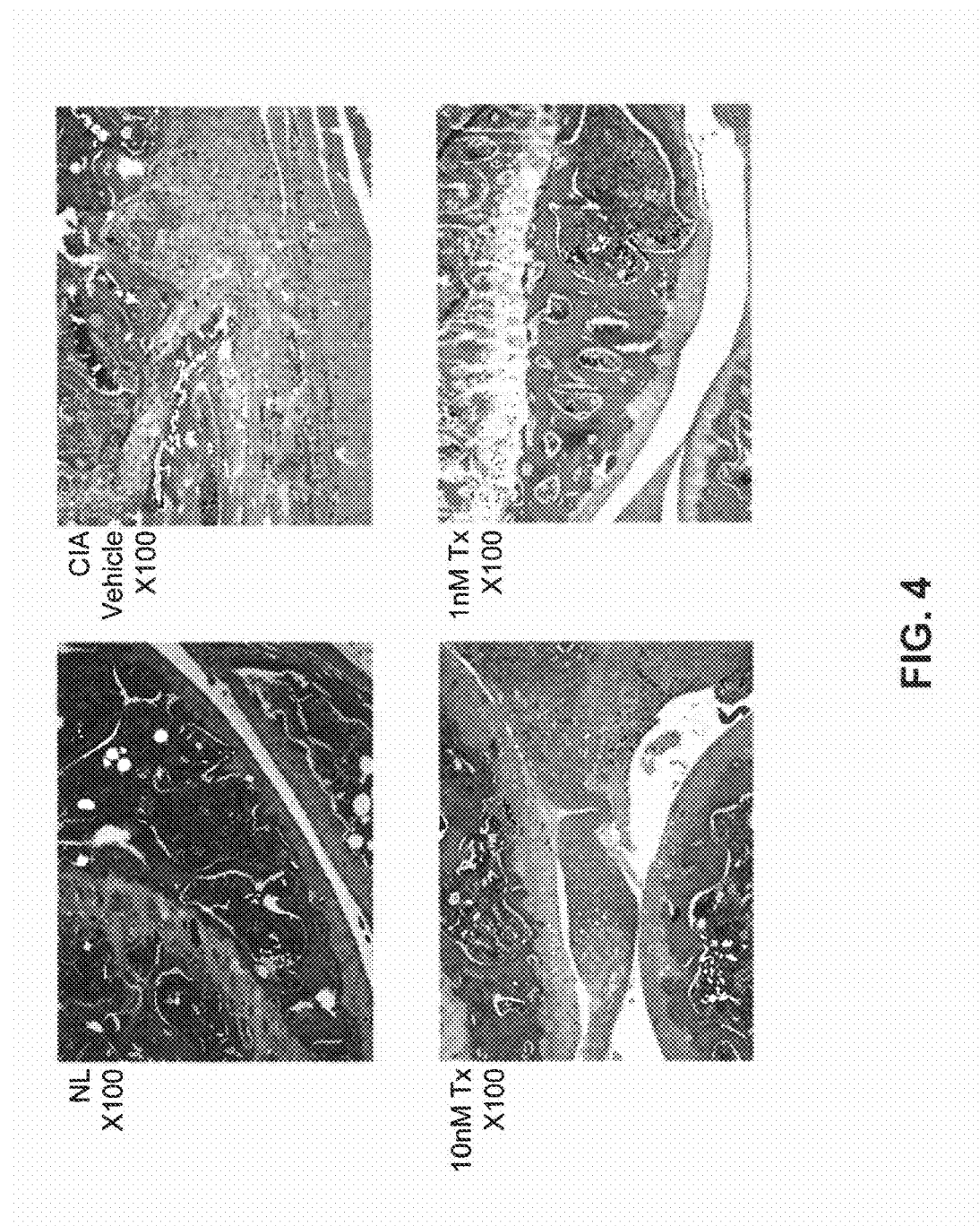
FIG. 4 shows a histopathogical profile for confirming a remedial value of rheumatoid arthritis.

In FIG. 4, the histopathological profile for confirming the effectiveness of the rheumatoid arthritis treatment was shown. As the result confirmed through the normal control group (NL), the CIA control group (CIA vehicle), and the 10 nM peptide and 1 nM peptide treated group (Tx), the erosion and permeation by more significant edema and inflammation were shown in cells of the CIA control group compared to the normal control group, and such damages of the cells were decreased in the peptide treatment group.

Result of the First Experiment

Figure 5:
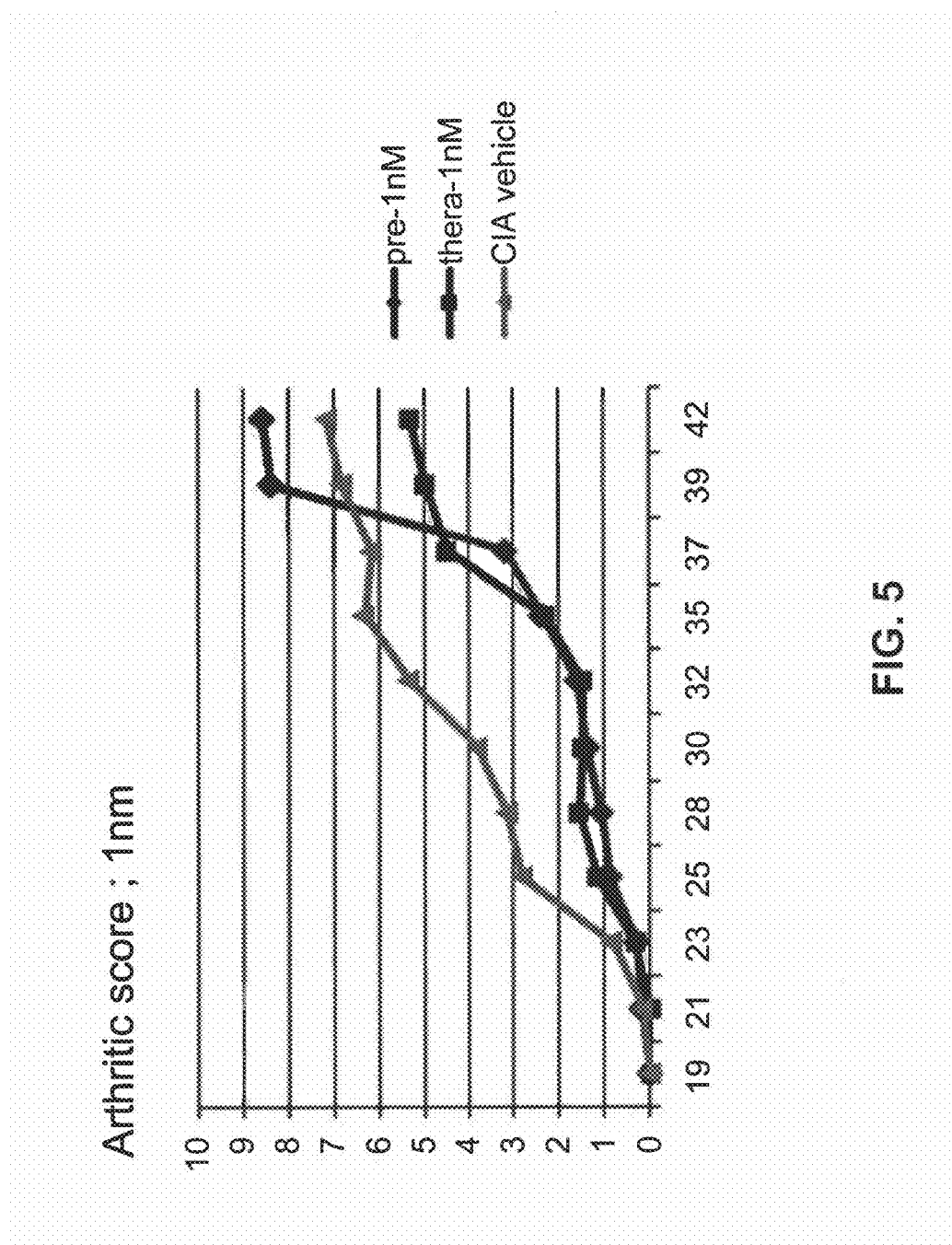
FIG. 5 shows a result of the first experiment that presents rheumatoid arthritis index of a control group, a 1 nM primary treatment group and a 1 nM late treatment group by a graph.
Figure 6:
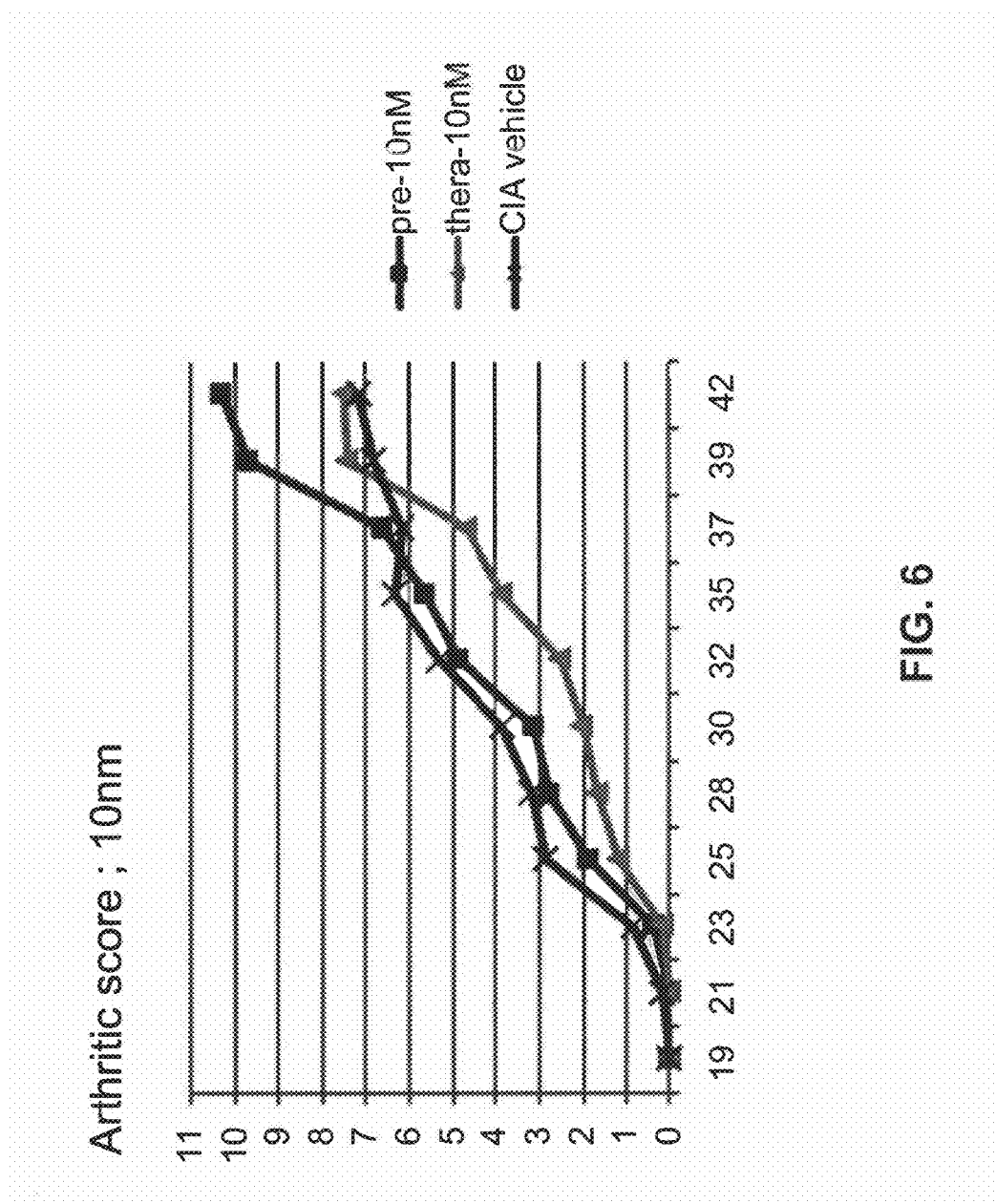
FIG. 6 shows a result of the first experiment that presents rheumatoid arthritis index of a control group, a 10 nM primary treatment group and a 10 nM late treatment group by a graph.
Figure 7:
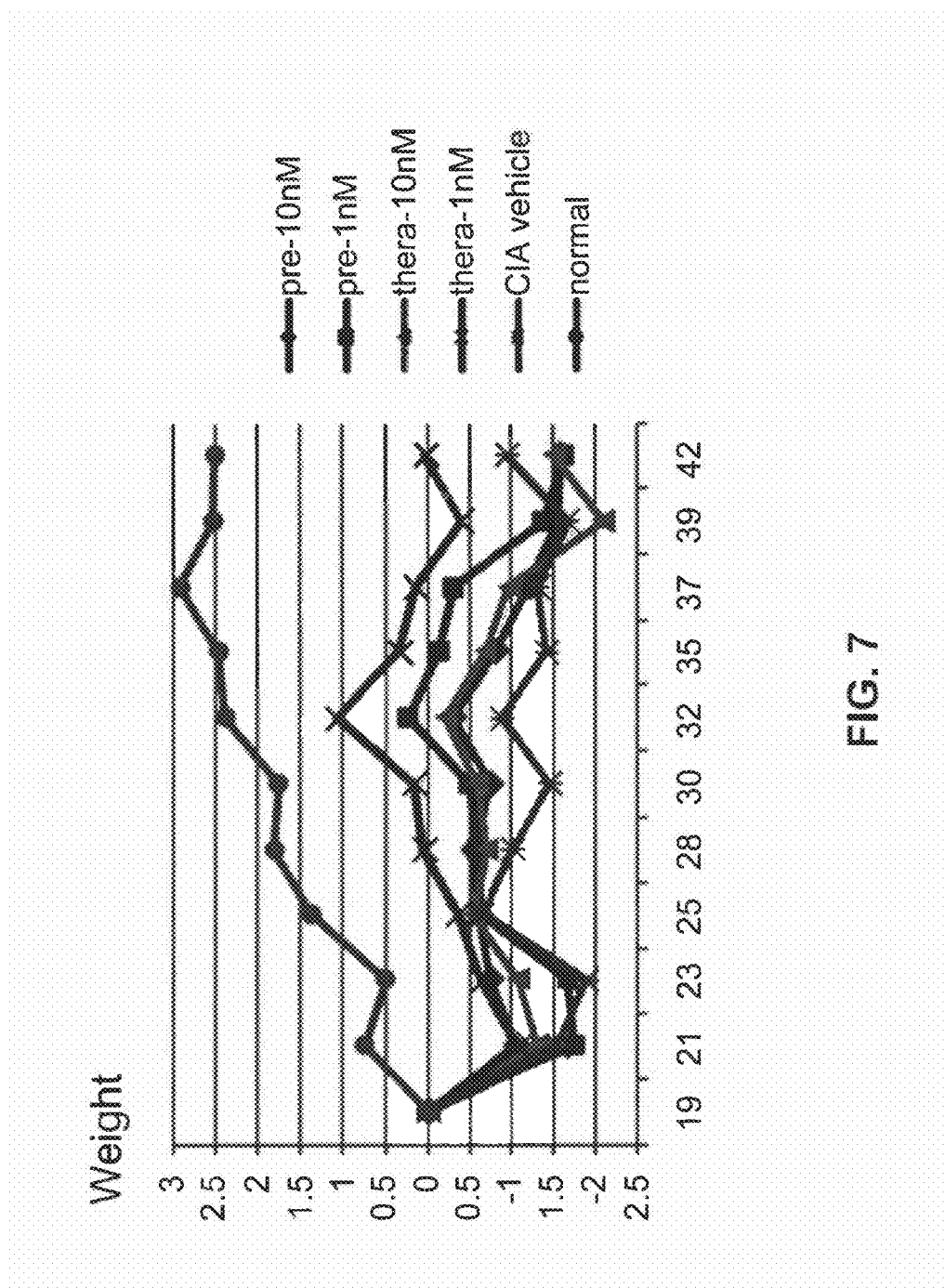
FIG. 7 shows changes in body weight of a control group and a treatment group, wherein Y axis value indicates a body weight changes by using a unit of gram. X axis value indicates treatment and time elapse.
Figure 8:
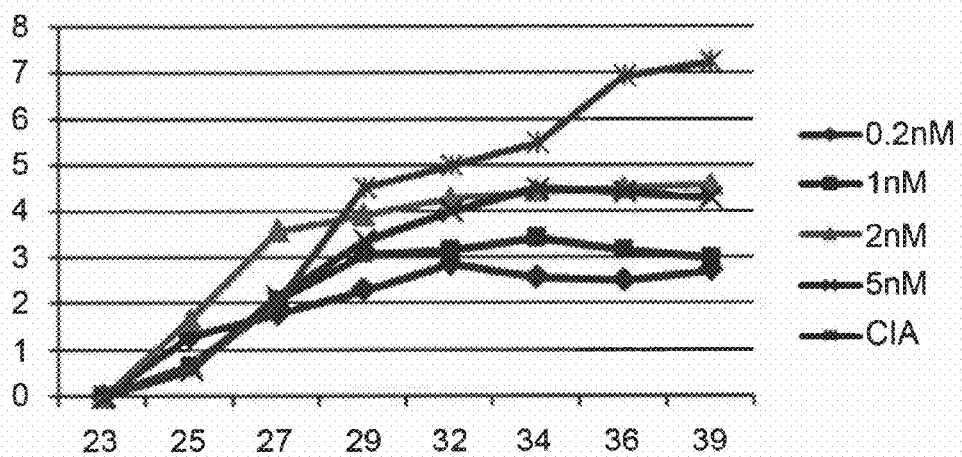
FIG. 8 shows a result of the second experiment that present rheumatoid arthritis index of a control group and 0.2 nM, 1 nM, 2 nM and 5 nM treatment groups (upper graph), and picturizes a more effectively appearing result of a low-concentration (0.2 nM, 1 nM) peptide treatment separately (lower graph).
Figure 8:
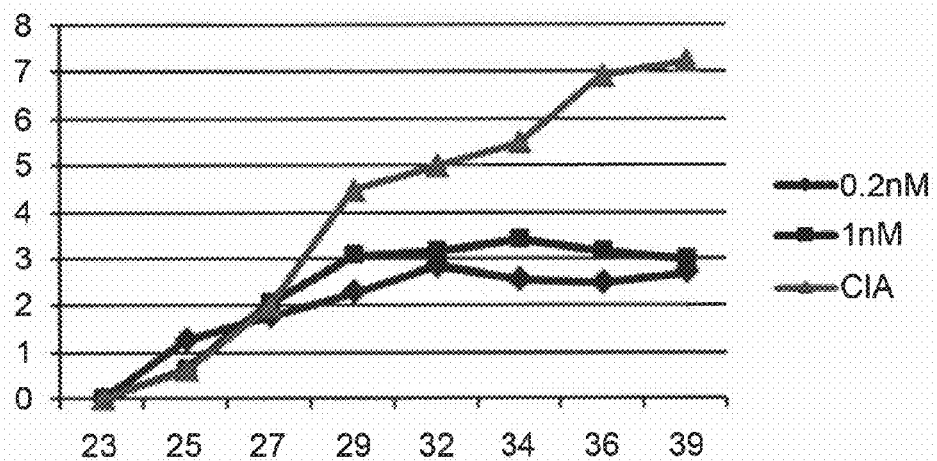

The preventive group (pre-1 nM and pre-10 nM) appeared effective to decreasing rheumatoid arthritis until day 36 but after then the effectiveness vanished. The therapeutic group (thera-1 nM and thera-10 nM) showed the decreasing arthritis effect in whole period but the 10 nM group showed the more effect than the 1 nM group. Also, the preventive group and the therapeutic group showed increased body weights compared to the CIA control group (see FIG. 5 to FIG. 7).

Result of the Second Experiment

Figure 9:
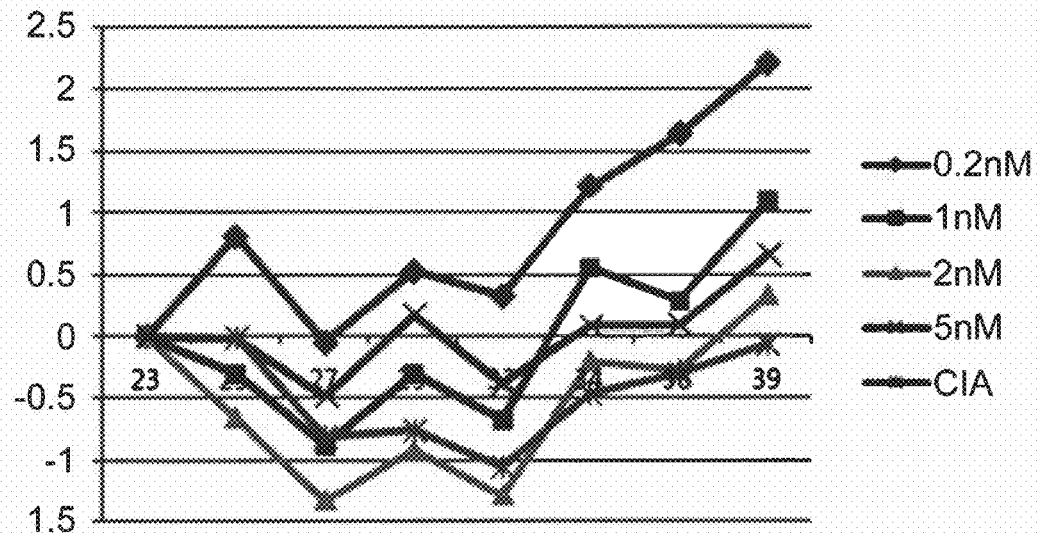
FIG. 9 shows a result of the second experiment that present a change of weight of a control group and 0.2 nM, 1 nM, 2 nM and 5 nM treatment groups (upper graph), and picturizes a more effectively appearing result of a low-concentration (0.2 nM, 1 nM) peptide treatment separately (lower graph).
Figure 9:
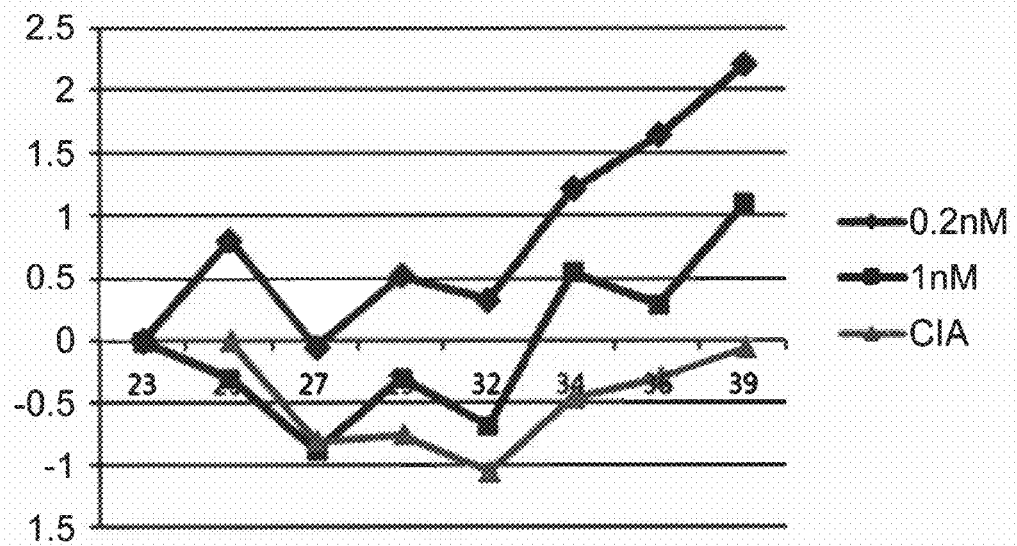

When the peptide treatment group of each concentration compared with the CIA control group, the peptide treatment group appeared to decrease the arthritis index in whole period. Also, when the body weights were measured, increased body weight was confirmed at the low-level peptide treatment group compared to the CIA control group (see FIG. 9).

As summarizing the result of the first and second experiments mentioned above, the administration of 1 nM peptide was more effective than the 1 nM peptide having lower level, and the therapeutic group treated after second inducement was more effective to inhibit rheumatoid arthritis than the preventive group. Also, in a result of measuring the change of the body weight in each group, decreased body weight in the therapeutic group of the 1 nM peptide treatment is lower than any other group, and this is also the effect of inhibiting arthritis.

Example 5

Toxicity Test (1) Cell Culture

HeLa cell line was purchased from ATCC, The HeLa cell line was maintained in MEM supplemented with 10% fetal bovine serum (Invitrogen, USA), Earle's salts, non-essential amino acids, sodium pyruvate, 100 ug/ml penicillin and 100 units/ml streptomycin, and then incubated at 37° C., 5% $CO_2$.

(2) Cell Viability and Toxicity Analysis

Figure 10:
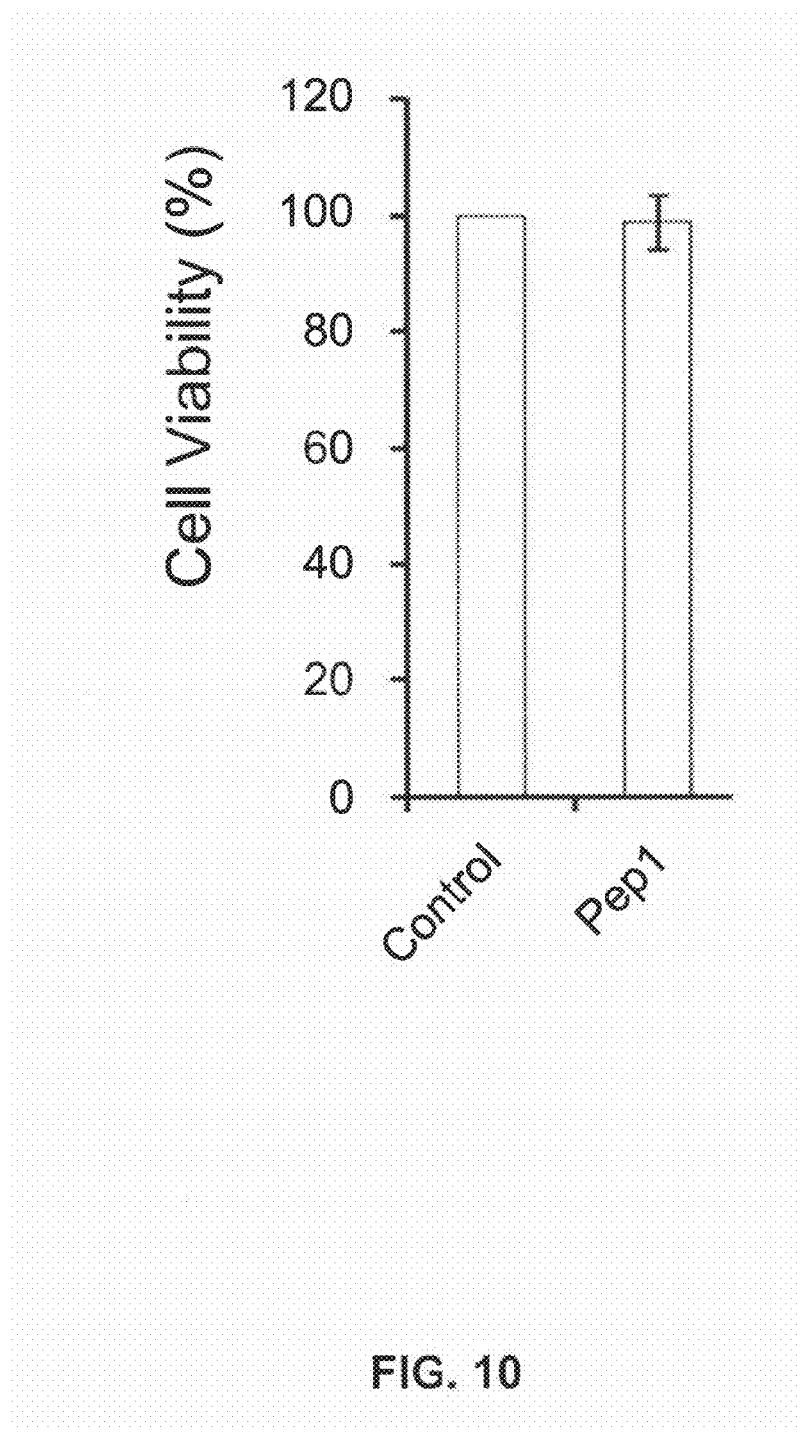
FIG. 10 shows a result of a toxicity test within HeLa cells.

The cells were seeded into 96-well plates and added to each well for medium supplemented with 10% fetal bovine serum (Invitrogen, USA), 100 ug/ml penicillin and 100 units/ml streptomycin. The cells were cultured in 37° C., 5% $CO_2$ for 12 h incubator. After incubated, plates washed by PBS, and added MEM (Minimum essential medium) for starvation during 1 h. The 20 μM of PEP 1 with 100 μL of the aqueous solution were added to each well, and then the cells were incubated at 37° C. for 24. After incubated, the cell viability and toxicity were evaluated using an MIT assay. The result is shown in FIG. 10.

The invention claimed is:

1. A method for treatment of rheumatoid arthritis comprising administering to a subject in need thereof an effective amount of the isolated peptide of SEQ ID NO: 1.

2. The method according to claim 1, wherein the peptide is administered in a single dose at a concentration of 0.001 ng/kg to 1 ng/kg.

3. The method according to claim 1, wherein the peptide is administered in a single dose at a concentration of 0.01 ng/kg to 0.4 ng/kg.

4. The method according to claim 1, wherein the peptide is administered once daily for 1 to 5 days.

5. The method according to claim 1, wherein the peptide is administered 1 to 3 times a day.

6. The method of claim 1, wherein the peptide is administered at a daily dose of 0.1 µg/kg to 1.0 g/kg.

7. The method of claim 6, wherein the peptide is administered 1 to 3 times daily.

8. A method for treatment of rheumatoid arthritis comprising administering to a subject in need thereof a composition comprising the isolated peptide of SEQ ID NO: 1.

9. The method of claim 8, wherein the composition is administered through oral, rectal, transdermal, intravenous, intramuscular, intraperitoneal, in the bone marrow, epidural, or subcutaneous means.

10. The method of claim 8, wherein the composition comprises 0.1 µg/mg to 1 mg/mg of the isolated peptide.

11. The method according to claim 8, wherein the peptide is administered in a single dose at a concentration of 0.001 ng/kg to 1 ng/kg.

12. The method according to claim 8, wherein the peptide is administered in a single dose at a concentration of 0.01 ng/kg to 0.4 ng/kg.

13. The method according to claim 8, wherein the peptide is administered once daily for 1 to 5 days.

14. The method according to claim 8, wherein the peptide is administered 1 to 3 times a day.

15. The method of claim 8, wherein the peptide is administered at a daily dose of 0.1 µg/kg to 1.0 g/kg.

16. The method of claim 15, wherein the peptide is administered 1 to 3 times daily.

* * * * *